United States Patent
Kiraly et al.

(10) Patent No.: US 12,032,658 B2
(45) Date of Patent: Jul. 9, 2024

(54) METHOD AND SYSTEM FOR IMPROVING CANCER DETECTION USING DEEP LEARNING

(71) Applicant: GOOGLE LLC, Monntain View, CA (US)

(72) Inventors: Atilla Kiraly, Mountain View, CA (US); Shravya Shetty, Mountain View, CA (US); Sujeeth Bharadwaj, Mountain View, CA (US); Diego Ardila, Mountain View, CA (US); Bokyung Choi, Mountain View, CA (US)

(73) Assignee: Google LLC, Mountain View, CA (US)

( * ) Notice: Subject to any disclaimer, the term of this patent is extended or adjusted under 35 U.S.C. 154(b) by 665 days.

(21) Appl. No.: 17/055,313

(22) PCT Filed: Nov. 20, 2018

(86) PCT No.: PCT/US2018/061956
§ 371 (c)(1),
(2) Date: Nov. 13, 2020

(87) PCT Pub. No.: WO2019/245597
PCT Pub. Date: Dec. 26, 2019

(65) Prior Publication Data
US 2021/0225511 A1    Jul. 22, 2021

Related U.S. Application Data

(60) Provisional application No. 62/726,178, filed on Aug. 31, 2018, provisional application No. 62/686,541, filed on Jun. 18, 2018.

(51) Int. Cl.
*G06T 7/11* (2017.01)
*G06F 18/213* (2023.01)
(Continued)

(52) U.S. Cl.
CPC .......... *G06F 18/254* (2023.01); *G06F 18/213* (2023.01); *G06F 18/2415* (2023.01);
(Continued)

(58) Field of Classification Search
CPC . G06T 7/0012; G06T 7/11; G06T 7/73; G06T 2207/10081; G06T 2207/20076;
(Continued)

(56) References Cited

U.S. PATENT DOCUMENTS

2006/0018524 A1   1/2006   Suzuki et al.
2011/0142301 A1*  6/2011   Boroczky .............. G16Z 99/00
                                                              382/128
(Continued)

OTHER PUBLICATIONS

Smith et al. "Weak Segmentations and Ensemble Learning to Predict Semantic Ratings of Lung Nodules." 12th International Conference on Machine Learning and Applications, Dec. 4, 2013, pp. 519-524 (Year: 2013).*

(Continued)

*Primary Examiner* — Jon Chang
(74) *Attorney, Agent, or Firm* — McDonnell Boehnen Hulbert & Berghoff LLP

(57) ABSTRACT

A method and system to generate a probabilistic prediction of the presence/absence of cancer in longitudinal and current image datasets, and/or multimodal image datasets, and the location of the cancer, is described. The method and system uses an ensemble of deep learning models. The ensemble includes a global model in the form of a 3D convolutional neural network (CNN) extracting features in the datasets indicative of the presence of cancer on a global basis. The ensemble also includes a two-stage prediction model which includes a first stage or detection model which identifies cancer detection candidates (different cropped volumes of 3D data in the a dataset containing candidates which may be cancer) and a second stage or probability model which (Continued)

incorporates the longitudinal datasets (or multimodal images in a multimodal dataset) and the extracted features from the global model and assigns a cancer probability p to each of the cancer detection candidates. An overall prediction of probability of cancer is obtained from the probabilities assigned by the second stage model, e.g., using a Noisy-OR approach.

33 Claims, 14 Drawing Sheets

(51) Int. Cl.
*G06F 18/2415* (2023.01)
*G06F 18/25* (2023.01)
*G06N 3/04* (2023.01)
*G06N 3/08* (2023.01)
*G06N 20/20* (2019.01)
*G06T 7/00* (2017.01)
*G06T 7/73* (2017.01)
*G16H 50/20* (2018.01)

(52) U.S. Cl.
CPC ............... *G06N 3/04* (2013.01); *G06N 3/08* (2013.01); *G06N 20/20* (2019.01); *G06T 7/0012* (2013.01); *G06T 7/11* (2017.01); *G06T 7/73* (2017.01); *G16H 50/20* (2018.01); *G06T 2207/10081* (2013.01); *G06T 2207/20076* (2013.01); *G06T 2207/20081* (2013.01); *G06T 2207/20084* (2013.01); *G06T 2207/20132* (2013.01); *G06T 2207/30061* (2013.01); *G06T 2207/30096* (2013.01); *G06V 2201/031* (2022.01)

(58) Field of Classification Search
CPC . G06T 2207/20081; G06T 2207/20084; G06T 2207/20132; G06T 2207/30061; G06T 2207/30096; G06V 2201/031; G06V 2201/03; G06F 18/254; G06F 18/213; G06F 18/2415; G06N 3/04; G06N 3/08; G06N 20/20; G16H 50/20
See application file for complete search history.

(56) References Cited

U.S. PATENT DOCUMENTS

2017/0018075 A1   1/2017  Middlebrooks et al.
2018/0075628 A1*  3/2018  Teare .................. G06V 10/454
2018/0338741 A1* 11/2018  Lyman ................. G16H 10/60

OTHER PUBLICATIONS

Antonelli et al. "A Multi-Classifier System for Pulmonary Nodule Classification." 21st IEEE International Symposium on Computer-Based Medical Systems, Jun. 17, 2008, pp. 587-589 (Year: 2008).*
The International Search Report (ISR) with Written Opinion for PCT/US2018/061956 dated Mar. 14, 2019, pp. 1-18.
Alakwaa, Wafaa et al. "Lung Cancer Detection and Classification with 3D Convolutional Neural Network (3D-CNN)" International Journal of Advanced Computer Science and Applications (2017) vol. 8(8), pp. 409-417.
Suk, H. et al. "Hierarchical feature representation and multimodal fusion with deep learning for AD/MCI diagnosis" NeuroImage 101 (2014), pp. 569-582.
Cole, James H. et al. "Predicting brain age with deep learning from raw imaging data results in a reliable and heritable biomarker" NeuroImage 163 (2017), pp. 115-124.
Fan, Lei et al. "Lung Nodule Detection Based on 3D Convolutional Neural Networks" International Conference on the Frontiers and Advances in Data Science (FADS) (2017), pp. 7-10.
Szegedy, Christian et al. "Rethinking the Inception Architecture for Computer Vision" CORR (ARXIV), vol. abs/1512.00567v3, (2015), pp. 1-10.
Sundararajan, Mukund et al. "Axiomatic Attribution for Deep Networks" arxiv.org, Cornell University Library, 201 OLIN Library Cornell University Ithaca, NY 14853, (Mar. 4, 2017), XP080754192.

* cited by examiner

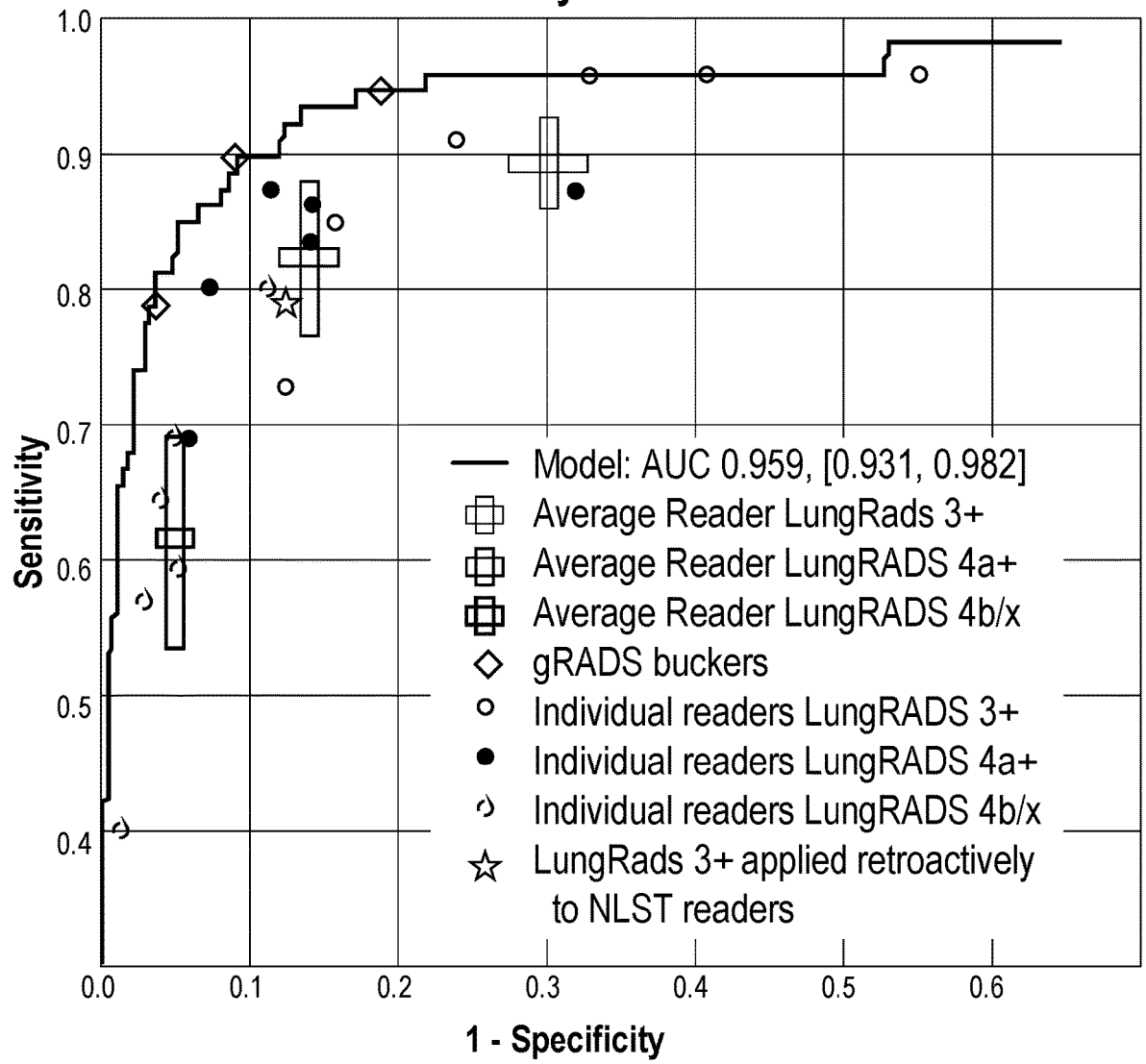

Fig. 8A
Fig. 8B
Fig. 8C
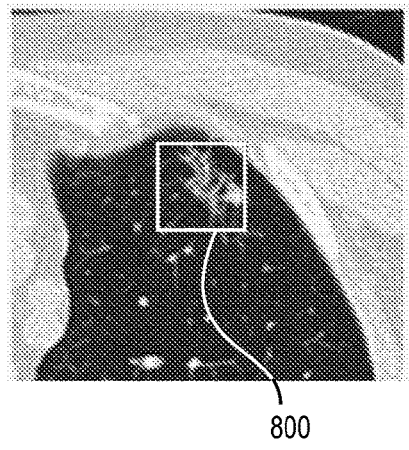
800
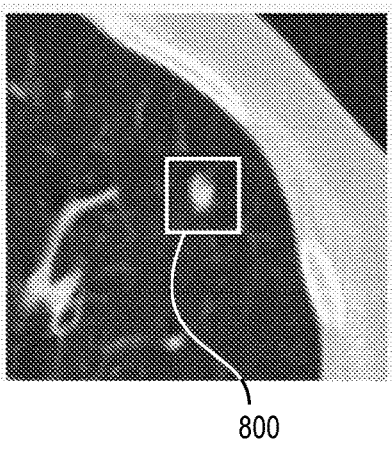
800
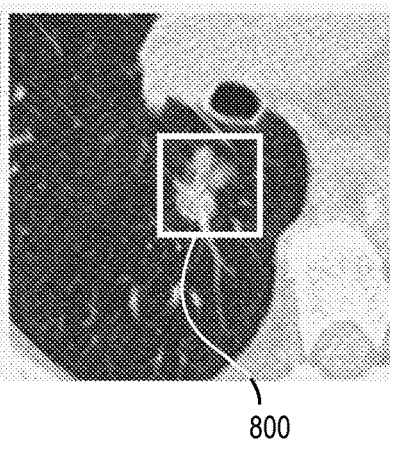
800
Fig. 9A
Fig. 9B
Fig. 9C
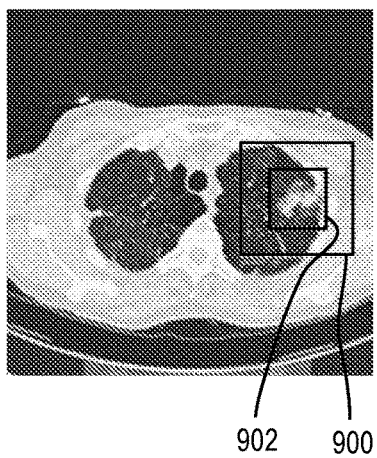
902  900
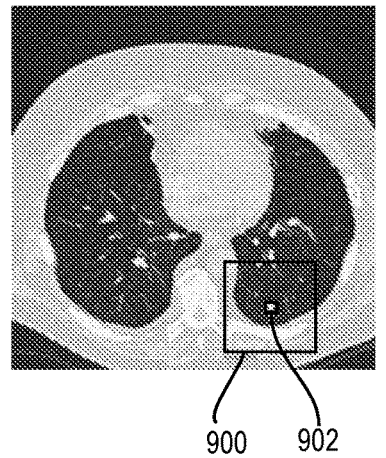
900  902
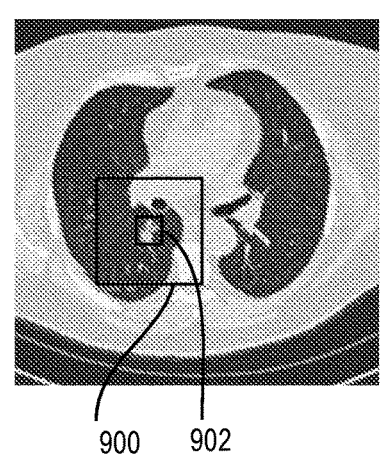
900  902

Fig. 10A
Fig. 10B
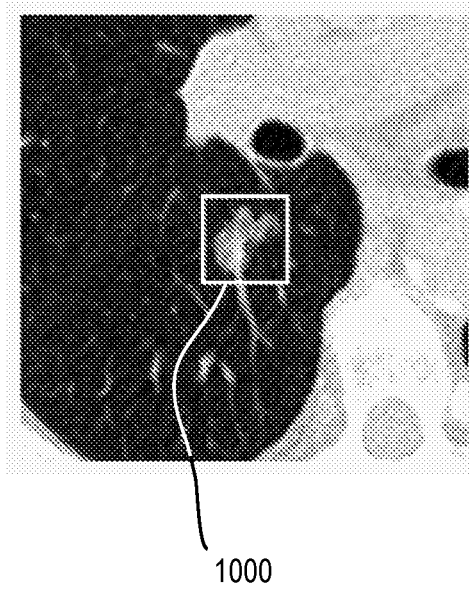
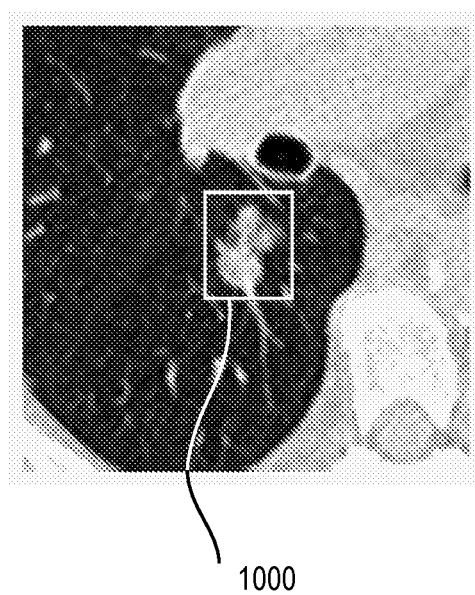

METHOD AND SYSTEM FOR IMPROVING CANCER DETECTION USING DEEP LEARNING

PRIORITY

This application claims the benefit of priority to U.S. provisional application serial no. 62/686,541 filed Jun. 18, 2018 and U.S. provisional application Ser. No. 62/726,178 filed Aug. 31, 2018.

BACKGROUND

This disclosure relates to a method and system for improving cancer detection and screening. The method is suitable for use with a variety of imaging datasets, including, for example, computed tomography (CT) datasets for lung cancer detection from CTs, and multimodal magnetic resonance imaging (MRI) for prostate cancer detection. The features of this disclosure can be applied in the context of low dose chest CT (LDCT) datasets, as well as general lung cancer detection from diagnostic chest CT datasets. The method and system may be implemented using deep learning methods.

Longitudinal and multimodal imaging techniques help improve cancer screening diagnosis. "Longitudinal imaging" refers to prior patient images being available for comparison to a current or most recent image in detecting and diagnosing cancer. "Multimodal MRI" is used to refer to multiple pulse-sequences taken during a single Magnetic Resonance Imaging (MRI) study. The term "multimodal imaging" is also used to refer to obtaining different types of images of a subject, such as MRI. CT scans, and positron emission tomography (PET), and such images which may or may not be obtained at the same time.

Typically, interpretation of imaging datasets is manually or semi-automatically performed by radiologists comparing the same region of the image across multiple time points or modalities. Automated approaches using deep learning can offer the ability to identify subtle cues across multiple images to identify and classify cancer. We present a general approach for incorporating longitudinal or multimodal imaging for the purposes of cancer detection and classification.

In the following description, the topic of lung cancer screening from LDCT images is presented. However, the approach described can generalize to other cancer topics, such as for example multimodal MRI for prostate cancer detection and classification.

By way of background, low-dose screening CT is part of the recommended guidelines for early detection of lung cancer for current and prior smokers ages 56-80. As a result of the National Lung Cancer Screening Trial (NLST), where patients were screened once a year for cancer using CT or X-ray, it was demonstrated that patients in the CT group had less mortality as compared to patients in the X-ray group. The American College of Radiology (ACR) has published the Lung CT Screening Reporting & Data System (Lung-RADS)™ guidelines for interpretation and management of low-dose lung cancer screening CT cases, basing evaluation of images on a variety of findings including: presence and absence of lung nodules; nodule size and density; nodule morphology; and secondary signs of neoplasm (eg. lymphadenopathy). In the context of lung cancer detection generally from CT scans, the Fleischner Society guidelines describe criteria for identification and characterization of pulmonary nodules, which may or may not be cancerous. Manually designed guidelines like Lung-RADS and the Fleischner guidelines offer a variety of advantages over subjective evaluation of imaging studies, including greater consistency, standardization, and typically improved overall performance. However, these systems are inherently limited by the criteria that define them, leaving opportunities for more complex analytical systems to additively improve performance, potentially in both sensitivity and specificity.

A variety of software devices are cleared or approved by the US Food and Drug Administration (FDA) for enhanced detection of lung nodules in lung CT images (screening, diagnostic, or otherwise). These systems are generally optimized to improve radiologist reader sensitivity for finding nodules, while minimizing costs to specificity, thereby falling into the category computer-aided detection, or CADe. Detectors generally highlight small nodules (often <1 cm) that might be otherwise missed, and usually highlight multiple potential areas containing nodules, leaving the clinical decision to the radiologist. In recent years, computer-aided diagnosis, or CADx, utilized for deeper assessment that drives diagnosis, has gained greater Interest and even first clinical approvals in other areas of radiology, though not yet in lung cancer. In particular, deep learning platforms hold promise to rapidly develop new algorithms based on clinically-validated endpoints, allowing these systems to determine their own independent pathways to clinical conclusions, giving enhanced performance and potentially new clinical insights. Deep learning approaches offer the potential to automate detailed evaluation, pick up on subtle holistic imaging findings that are otherwise unreported, and unify the methodology for grading and evaluating CT scans.

Several papers are directed to lung nodule detection and diagnosis from CT scans using deep learning, including Xiaojie Huang, at al., *Lung Nodule Detection in CT Using 3D Convolutional Neural Networks*, The 2017 IEEE International Symposium on Biomedical Imaging. April 2017; Francesco Ciompi at al., *Towards automatic pulmonary nodule management in lung cancer screening with deep learning*, Scientific Reports 7, article no. 46479 Apr. 17, 2017; Wenqing Sun at al., *Computer Aided lung cancer diagnosis with deep learning*. Medical Imaging 2016, Proc. of SPIE vol. 9785 (March 2016); Albert Chon at al., *Deep Convolutional Neural Networks for Lung Cancer Detection*, Stanford University Reports (2017), www.cs231n.stanford.edu/reports/2017/pdfs/518.pdf, and Wafaa Alakwaa, et al., *Lung Cancer Detection and Classification with 3D Convolutional Neural Network (3D-CNN)*, International Journal of Advanced Computer Science and Applications, vol. 8 no. 8. pp 409.417 (2017). The art also describes the situation where a nodule has already assumed to have been detected and a prediction of the risk of the malignancy is generated.

SUMMARY

In one aspect, we describe a method and system to generate a probabilistic prediction of the presence/absence of lung cancer in a CT data set, and the location of the cancer, using an ensemble of models, such as deep learning models. The ensemble of models includes a global predictive model in the form of a 3D convolutional neural network (CNN) which is trained to predict, on a global basis (i.e., over the entire CT volume), the probability of presence and location of cancer in lung tissue in a CT data set. The global model may therefore take as input the entire CT volume and output a global prediction of the presence of cancer in the area of interest represented in the CT volume. This output of this global model represents an end-to-end prediction of cancer in a single model over the entire CT volume. Optionally, this global model includes a feature to isolate lung tissue from non-lung tissue in a chest CT data set and predicts the probability and location of the presence of cancer in just the lung tissue.

The ensemble also includes a two-stage prediction model which includes a first stage or detection model which identifies cancer detection candidates (different cropped volumes of 3D data in the CT data set containing candidates which may be cancer, not just merely nodules, which may or may not be cancerous) and a second stage or probability model which assigns a cancer probability p to each of the cancer detection candidates. The detection and probability models of the two-stage prediction model can be based on convolutional neural networks as well. The detection model may therefore process the CT data set to generate candidate volumes of the CT data set representing portions of the imaged region of interest and the probability model may process the candidate volumes of the CT data set to determine a probability that the candidate volume represents a portion of the imaged region of interest that is indicative of the patient having cancer, for example a portion that includes one or more cancer cells.

In practice, there may be more than one, such as three or five, different second stage probability models, e.g., models A, B, C, D, etc., each with its own set of parameters, and each making a prediction of the probability of cancer in each of the detection candidates. Possible differences in parameters which define such second stage models include 1) different patch sizes (i.e., varying size volumes of cropped 3D data in the data set, in order to detect cancer at different scales), 2) different optimization parameters used during learning, such as learning rate, 3) taking models at multiple points during the course of training (weights change over the course of training so each model would have slightly different predictions); 4) different parameters as a result of data augmentation during training, and 5) different model architectural settings, such as the depth, kernel size and number of convolutions for each model. In particular, in one implementation the training data may be modified to generate additional training data during training in order to expose the model to more variation. For example, small random rotations may be applied to the input volumes to generate additional training volumes. This data augmentation has parameters which may vary among members of the ensemble, for example the amount of random rotation.

The prediction probability generated by the global model and each of the second stage probability models are then combined, for example, in accordance with some defined function $f$, or algorithm, to generate an overall or final probability prediction (e.g., a "malignancy likelihood score," typically presented in terms of percentage from 0 to 100) of cancer/no cancer in the CT data set and location of the possible cancer. In one configuration, these probabilities can also be used in a novel scoring method, either to approximate existing scoring schemas or by defining a new one. The defined function $f$ could consist of an averaging of the predicted probabilities of the global model and each the final or total probability of each of second stage models, i.e., computed over all the cancer detection candidates, or in the form of a weighted average.

Thus, in one aspect, a method is provided for improving lung cancer screening and detection from a computed tomography data set obtained for a patient. The method includes the steps of a) supplying the data set to a global predictive model comprising a three-dimensional deep convolutional neural network trained to predict at least the probability of the presence of cancer in lung tissue in the data set on a global basis; b) supplying the data set to a two-stage prediction model, the two-stage prediction model comprising 1) a first stage detection model detecting the location of one or more three-dimensional cancer candidates within the data set, and 2) a second stage probability model operating on the one or more three-dimensional cancer candidates detected by the first stage detection model and assigning a cancer probability p to each of the three-dimensional cancer candidates; and c) generating data representing (1) an overall prediction of the probability of cancer in the data set using both the prediction of the global predictive model and the cancer probabilities p assigned by the second stage probability model to each of the three-dimensional cancer candidates, and (2) the location of cancer in the data set, wherein the location of cancer is determined by either the global predictive model or the two-stage prediction model.

In another aspect, a computer-implemented system for improving lung cancer screening and detection from a computed tomography data set obtained for a patient is disclosed. The system includes a) a global predictive model comprising a three-dimensional deep convolutional neural network trained to predict at least the probability of the presence of cancer in lung tissue in the data set on a global basis: b) a two-stage prediction model, the two-stage prediction model comprising 1) a first stage detection model detecting one or more three-dimensional cancer candidates within the data set, and 2) a second stage probability model operating on the one or more three-dimensional cancer candidates detected by the first stage detection model and assigning a cancer probability p to each of the three-dimensional cancer candidates; and c) a computer system executing code for generating data representing (1) an overall prediction of the probability of cancer in the data set using the prediction of the global predictive model and the cancer probabilities p assigned by the second stage probability model to each of the three-dimensional cancer candidates, and (2) the location of cancer in the data set. The location of cancer is determined by either the global predictive model or the two-stage prediction model.

In one configuration, there are a plurality of second stage models which take the form of deep convolutional neural networks each having an intermediate convolutional layer associated with a feature map. The global probability model includes an intermediate convolutional layer associated with a feature map. In step c) the overall prediction of the probability of cancer in the data set is obtained by either (1) appending the feature maps from the second stage models to the feature map of the intermediate convolutional layer of the global model and generating the prediction from the global model, or (2) appending the feature map from the global model to the feature maps of the intermediate convolutional layer of the second stage models, and generating the prediction from the output of the second stage models.

In an aspect, a method for determining a probability of the presence of cancer in a region of interest of a patient from a computed tomography data set obtained for the patient is described. The method includes the steps of:
  a) processing the computed tomography data set using a predictive model (global predictive model) comprising a three-dimensional deep convolutional neural network trained to generate a global probability of the patient having cancer from the computed tomography data set.
  b) processing the computed tomography data set using a two-stage prediction model, the processing comprising:

1) processing the computed tomography data set using a detection model to generate one or more three-dimensional candidate volumes in the data set as candidate regions of interest representing one or more cancer cells, and
2) processing the one or more three-dimensional candidate volumes generated by the detection model to generate a probability for each of the three-dimensional candidate volumes, the probability for each of the three-dimensional volumes indicating a probability that the three-dimensional volume represents one or more cancer cells; and c) generating the probability of the patient having cancer using both the global probability of the patient having cancer and the probabilities for each of the three-dimensional candidate volumes.

Each aspect may optionally include one or more of the following features. The one or more three-dimensional cancer candidates are provided to a plurality of second stage probability models operating on the one or more three-dimensional cancer candidates detected by the first stage detection model, each of the second stage probability models assigning a cancer probability p to each of the three-dimensional cancer candidates, wherein each of the plurality of second stage probability models are characterized by different model parameters. The different model parameters are selected from the group of parameters consisting of 1) different volumes of cropped 3D data in the data set, 2) different optimization parameters used during learning, 3) taking models at different points during the course of training, 4) different parameters as a result of data augmentation during training and 5) different model architectural settings, such as the depth, kernel size and number of convolutions for each model. In step c) the overall probability comprises an average of the global probability generated by the global model, and the total probability for each of the candidates calculated by each of the plurality of second stage probability models. The global predictive model is trained to predict at least one of the following in addition to the probability of presence of cancer in the data set: a) cancer outcome; b) presence of nodules of a size at least 20 mm in two dimensions; c) probability of mortality within 5 years d) diagnosis of cancer within 2 years. The global model uses a base feature extractor to identify the presence of cancer in the data set and wherein the first stage detection model uses the base feature extractor. The first stage detection model and the second stage probability model comprise deep convolutional neural networks. The first stage detection model operates on the whole volume of the data set. The global prediction model further comprises a lung segmentation feature identifying tissue within the data set such that the prediction of probability of presence of cancer in the data set globally operates only within the identified lung tissue. In one configuration the methods places the overall prediction of the probability of cancer in the data set into a bucket of a risk stratification schema. The risk stratification schema approximates an existing risk stratification schema, such as Lung-RADS™.

In another aspect, a method for generating a deep learning system for increasing the specificity of lung cancer screening of computed tomography data sets is described. The method includes the steps of:
a) training a global predictive model in the form of a three-dimensional deep convolutional neural network to predict at least the probability of the presence of cancer in lung tissue in a computed tomography data set globally, wherein the training is performed on a body of computed tomography data sets with ground truth annotations indicating presence or absence of cancer;
b) training a first stage detection model for detecting one or more three-dimensional cancer candidates within the computed tomography data set;
c) training a plurality of second stage probability models operating on the one or more three-dimensional cancer candidates detected by the first stage detection model, each of which assign a cancer probability p to each of the three-dimensional cancer candidates, wherein each of the plurality of second stage probability models are characterized by different model parameters, and
d) defining an algorithm or function for combining the predictions of the global predictive model and the second stage probability model in an ensemble manner to generate an ensemble or overall prediction of the probability of cancer in a CT scan data set.

Each aspect may include one or more of the following features. The different model parameters are selected from the group of parameters consisting of 1) different volumes of cropped 3D data in the data set, 2) different optimization parameters used during learning, 3) taking models at different points during the course of training, 4) different parameters as a result of data augmentation during training and 5)) different model architectural settings, such as the depth, kernel size and number of convolutions for each model. The algorithm is an average calculation. The global predictive model is trained to predict at least one of the following in addition to the probability of presence of cancer in computed tomography data set: a) cancer outcome; b) presence of nodules of a size at least 30 mm in two dimensions; c) probability of mortality within 5 years d) diagnosis of lung cancer within 2 years. The global predictive model is further trained to segment lung tissue from non-lung tissue in a computed tomography data set. In one configuration the global model includes an attention mechanism, such as integrated gradients. In one configuration the method includes a risk stratification schema in the form of a plurality of buckets wherein the overall prediction of the probability of cancer in the data set is placed into one of the buckets in the risk stratification schema. The risk stratification schema approximates an existing risk stratification schema, such as Lung-RADS™.

It will be appreciated that aspects can be implemented in any convenient form. For example, aspects may be implemented by appropriate computer programs which may be carried on appropriate carrier media which may be tangible carrier media (e.g. disks) or intangible carrier media (e.g. communications signals). Aspects may also be implemented using suitable apparatus which may take the form of programmable computers running computer programs arranged to implement the invention.

It will be appreciated that aspects can be combined such that features described in the context of one aspect may be implemented in the context of another aspect.

Whilst the techniques are generally discussed in the context of lung cancer, it will be appreciated that the techniques may be applied to cancers other than lung cancer.

In addition, we describe in this document the incorporation of longitudinal and multimodal imaging in a novel deep learning framework for enhanced cancer detection and diagnosis. Partial or full automation facilitates the scaling of image-based screening to promote widespread accessibility. As will be appreciated from the following discussion, the systems and methods of this disclosure can be used when there is a set of longitudinal images, such as 3D volumetric datasets, of a given imaging modality, such as CT scan datasets. The systems and methods can also be used where there is a set of multimodal datasets, which may or may not include longitudinal (prior) imaging datasets of the subject. The methods and systems can also be extended to the situation where there is both longitudinal, and multimodal imaging datasets available for a given subject and they can all be combined in the deep learning framework described below to increase the accuracy of cancer detection and diagnosis.

In one aspect, we describe a method and system for generating a probabilistic prediction of the presence/absence of lung cancer in a medical image-based dataset consisting of recent (e.g., current) and longitudinal (prior) image datasets, and the location of the cancer, using an ensemble of deep learning models. The method includes the steps of:

a) supplying the recent and, optionally, the longitudinal datasets to a global predictive model comprising a three-dimensional deep convolutional neural network extracting features in the datasets indicative of the presence of cancer;

b) supplying the recent and longitudinal datasets to a two-stage prediction model, the two-stage prediction model comprising
  1) a first stage detection model detecting one or more cancer candidates within the current dataset, and
  2) a second stage probability model operating on the one or more three-dimensional cancer candidates detected by the first stage detection model and incorporating the longitudinal datasets and the extracted features from the global model and assigning a cancer probability p to each of the three-dimensional cancer candidates; and c) generating an overall prediction of the probability of cancer in the dataset from cancer probabilities p assigned by the second stage probability model to each of the three-dimensional cancer candidates.

Each aspect may optionally include one or more of the following features. In one configuration, the recent and longitudinal datasets are registered locally about the cancer candidates which are detected by the detection model in the two-stage model. In another possible configuration, the recent and longitudinal datasets are globally registered prior to the step of generating the predictions. In one embodiment, the datasets are comprised of Low Dose Lung CT imaging acquired for cancer screening. In another embodiment, the Lung CT images are acquired as a part of a diagnostic study. In another embodiment, the datasets are in the form of Magnetic Resonance Imaging (MRI) datasets acquired for cancer screening, or recent and longitudinal PET image datasets.

The following are additional optional features of the method. The one or more three-dimensional cancer candidates are provided to a plurality of second stage probability models. Each of the second stage probability models assigns a cancer probability p to each of the three-dimensional cancer candidates. In one possible configuration, each of the plurality of second stage probability models are characterized by different model parameters. However, for a single second stage model, shared weights are used in processing the one or more candidates. The different model parameters are selected from the group of parameters consisting of 1) different volumes of cropped 3D data in the dataset, 2) different optimization parameters used during learning, 3) taking models at different points during the course of training, 4) different parameters as a result of data augmentation during training and 5) different model architectural settings, such as the depth, kernel size and number of convolutions for each model. In step c) the overall probability comprises an average of the probabilities for each of the candidates calculated by each of the plurality of second stage probability models. In one configuration, the first stage detection model and the second stage probability model comprise deep convolutional neural networks. The first stage detection model operates on the whole volume of the dataset. In one possible configuration, the global model includes a lung segmentation feature identifying tissue within the dataset such that the extraction of features indicative of cancer operates only within the identified lung tissue. In one configuration the methods places the overall prediction of the probability of cancer in the dataset into a bucket of a risk stratification schema. The risk stratification schema approximates an existing risk stratification schema, such as Lung-RADS™.

The method is applicable by extension to other types of image datasets of a patient, and in particular multimodal images. In particular, in another aspect a method for medical image-based cancer screening and detection from a multimodal image-based dataset is described. The method includes the steps of:

a) supplying the multimodal dataset to a global predictive model comprising a three-dimensional deep convolutional neural network extracting features in the dataset indicative of the presence of cancer;

b) supplying the multimodal dataset to a two-stage prediction model, the two-stage prediction model comprising
  1) a first stage detection model detecting one or more cancer candidates within one of the images in the multimodal dataset (e.g., a 3D CT image dataset), and
  2) a second stage probability model operating on the one or more three-dimensional cancer candidates detected by the first stage detection model and other Images in the multimodal dataset (such as a PET image and an MRI image) and the extracted features from the global model and assigning a cancer probability p to each of the three-dimensional cancer candidates; and c) generating an overall prediction of the probability of cancer in the dataset from cancer probabilities p assigned by the second stage probability model to each of the three-dimensional cancer candidates It will be appreciated that aspects can be combined such that features described in the context of one aspect may be implemented in the context of another aspect.

Whilst the techniques are generally discussed in the context of lung cancer, it will be appreciated that the techniques may be applied to cancers other than lung cancer, such as prostate or breast cancer.

In another aspect of this disclosure, a method is further described for predicting if a patient is at risk of developing aging-related brain disease. The method makes use of a predictive model for brain age developed without domain knowledge from a data set of 30 images (e.g., structural magnetic resonance imaging (SMRI) or CT) of cognitively impaired subjects and normal subjects who belong to the same chronological age group. The method includes the steps of:

a) obtaining one or more 3D images from the patient and supplying the one or more 3D images to the predictive model;

b) generating a brain age prediction for the subject with the predictive model, and c) comparing the brain age prediction with the actual age of the patient, wherein if the brain age prediction is substantially greater than that of the actual age of the patient, the patient is identified as being at increased risk of developing aging-related brain disease.

BRIEF DESCRIPTION OF THE DRAWINGS

FIG. 3 is an illustration of a multi-scale feature extraction method of generating per-instance predictions for a given input cancer candidate 3D volume. The predictions per instance can be combined into a final prediction based on some function, examples of which are described below. Additionally, we can handle instances at different levels of a deep learning model, including pre-logit level concatenation of features, pre-pooling concatenation of feature maps, and so on.

FIG. 7A-7C are receiver operating characteristic area under the curve (AUC) plots showing performance of the system of FIG. 5 with current and without longitudinal image datasets, relative to retrospective comparison of Lung-RADS™ criteria by trained readers to the NLST dataset.

FIGS. 8A-8C are CT scan images of a patient with a box showing a region of interest detected by the two-stage model for which cancer probability is predicted.

FIGS. 9A-9C are CT scan images of a patient with a box showing a region of interest detected by the two-stage model for which cancer probability is predicted. Note that a large context around the nodule is available for the second stage model.

FIGS. 10A and 10B show the registration of a ROI in a prior and current CT scan image.

DETAILED DESCRIPTION

This document describes the development and implementation of a deep learning method for evaluation of lung cancer screening CT datasets obtained from patients, with the goals of generation of a prediction of the probability of presence/absence of cancer in the patient based upon the dataset, and if present, the cancer location in the CT dataset. The methods of this disclosure improve the specificity and sensitivity of lung cancer detection in CT datasets. In one possible embodiment, the system can be configured as a computer-based deep learning lung cancer detection and screening tool which can help trained radiologists in diagnosis and managing treatment of cancer patients.

In the following discussion of FIGS. 1-4, Section I, we will describe a general overview of our deep learning models and the use thereof with imaging datasets which do not include longitudinal or multimodal imaging datasets. With that overview and explanation in mind, the disclosure will then proceed in Section II to describe the use of an ensemble of deep learning models which use recent and longitudinal image datasets, or multimodal datasets, in conjunction with FIGS. 5-11.

Figure 1:
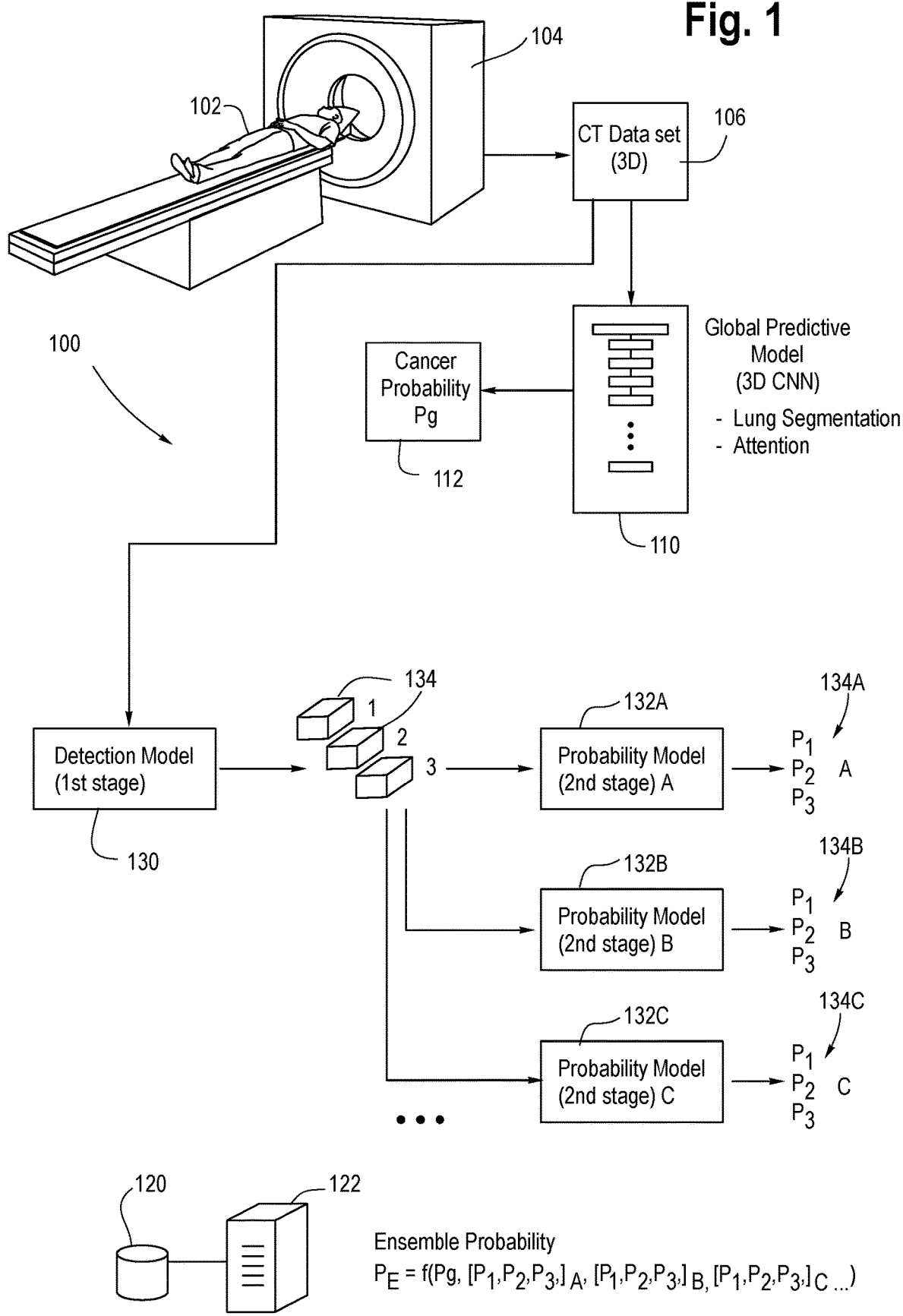
FIG. 1 is an illustration of our system and method for improving of lung cancer screening and detection from computed tomography datasets using deep learning, including a global predictive model, a first stage detection model, and one or more second stage probability models. The system of FIG. 1 could be deployed in a cloud environment in which the global and two stage predictive models are implemented remotely and return a final probability score indicative of the likelihood of cancer, and the location of the cancer in the dataset, to a clinic or office where the CT dataset is obtained. Alternatively, the system of FIG. 1 could be Implemented locally, i.e., with the computing resources and deep learning models located locally to the office or clinic.
Figure 5:
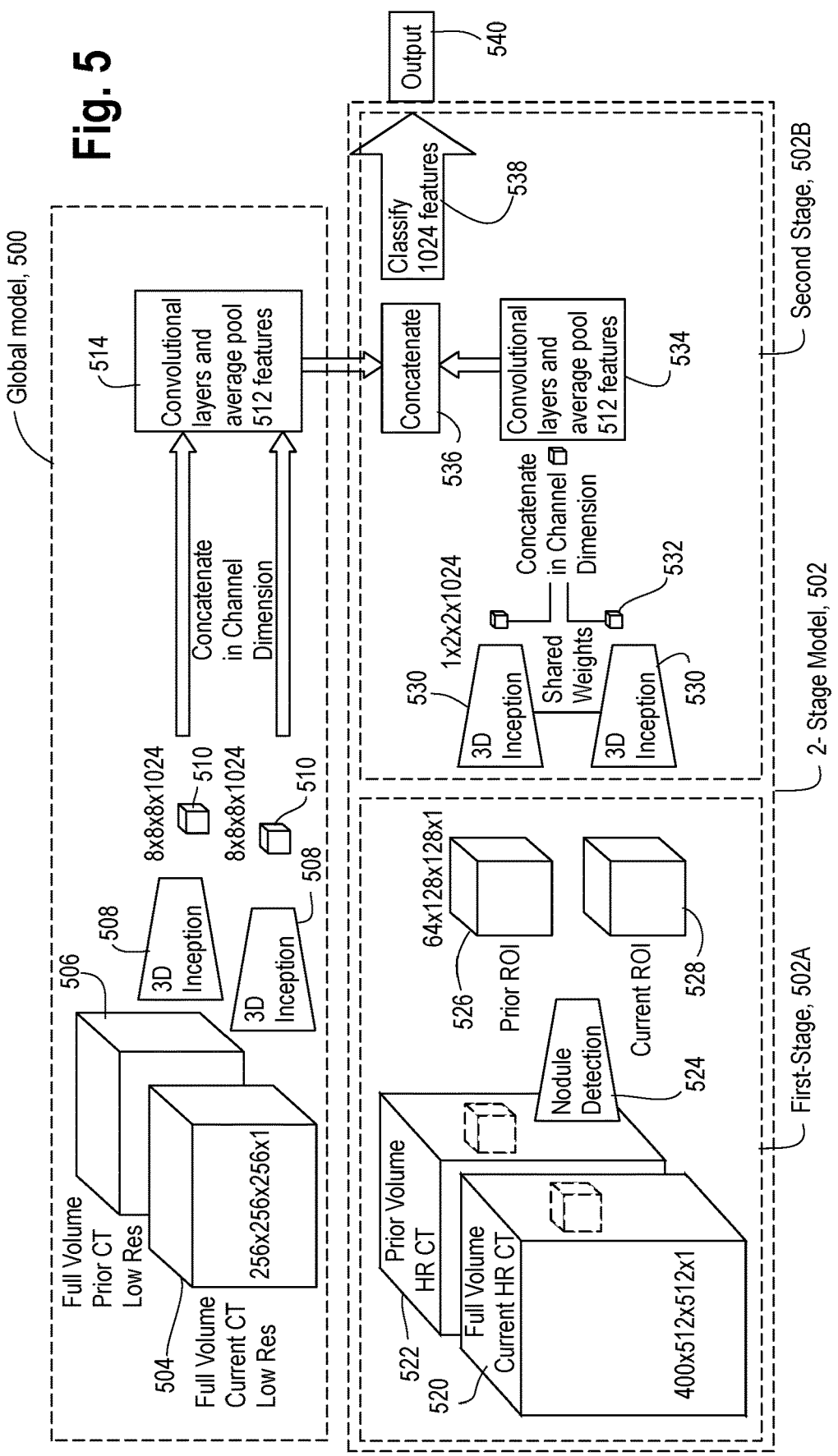
FIG. 5 is an illustration of a deep learning system for incorporating longitudinal images for performing detection and classification of medical image-based datasets.

An extension of the development of the global model of FIGS. 1 and 5 to SMRI brain images and development of brain age predictive model and use thereof to Identify patients as being at increased risk of age-related brain diseases is set forth in Section III of this document.

I. Overview, Ensemble of Models, and Use Thereof without Longitudinal or Multimodal Image Datasets (FIGS. 1-4)

For development and training of the models described in this disclosure, we analyzed the National Lung Screening Trial (NLST) dataset, inclusive of 42,943 CT studies from 14,863 patients, 620 of whom developed biopsy-confirmed cancer. Additional details regarding cases in the dataset are available through the National Institutes of Health (NIH) Cancer Data Access System [biometry.nci.nih.gov/cdas/learn/nlst/images/]: briefly, cases were acquired at low-dose from multiple institutions, slice thicknesses varied from 1.25 to 2.5 mm (greater slice thickness data from the NLST dataset was eliminated from consideration), and scanner vendors varied by site. Cases were split into three grouped sets: training (70%), tuning (15%) and test (15%). Steps were performed to ensure that cancer cases appeared in all three grouped sets, so the splitting of the cases was not completely random. Ground truth for presence of cancer was defined by determination of whether the patient was diagnosed with biopsy- or surgically-confirmed lung cancer during the screening year (i.e. true positive). "Negative" was defined by absence of cancer according to NLST results (patients in the trial had a median of 6.5 years follow-up). The dataset includes clinical data for the patients associated with the CT datasets, which were used to develop different binary classifications besides cancer/no-cancer in the global model, as explained below.

Our method is designed to assign a "malignancy likelihood score" (or ensemble probability $P_E$ below) on a 0-100% basis. This probability prediction can then be converted via thresholding to grouped Lung-RADS categories of 1 and 2 versus 3/4A and 4B, or other known alternative risk stratification buckets. Alternative, and potentially completely new risk categorization buckets can be defined from our ensemble predictions, as will be explained in further detail below.

At a high level, our approach to generating a cancer probability prediction from a CT dataset improves upon the prior art because it includes a global model that is trained to predict, on a global basis (i.e., over the entire CT volume), the probability of presence of cancer in lung tissue in a CT dataset. Optionally, the location of the cancer in the CT volume can be determined by the global model, e.g., through the use of attention mechanisms as described below. This global model is part of an ensemble of models, including a two-stage prediction model which includes a first stage or "detection" model that identifies 3D cancer candidates 1, 2, 3, . . . (cropped 3D volumes in the dataset) and second stage or "probability" model that generates a cancer probability p1, p2, p3, . . . for the cancer candidates identified by the first stage model. A final score or probability of cancer in the CT dataset is then obtained by combining the results from the global model and the cancer probabilities p generated by the second stage prediction models, e.g., by averaging the probabilities of the global model and an overall or total probability from second stage probability model over the cancer detection candidates. As noted, preferably there are a plurality of second stage probability models that are individually generating cancer predictions for each of the detection candidates, for example 4 or 5 of such second stage probability models, each having different parameters as explained below. The system and method generates data representing the overall or final prediction probability and the location of the cancer in the CT dataset.

FIG. 1 is an illustration of a system 100 for implementing our method for improving specificity of lung cancer screening computed tomography datasets using deep learning. A patient 102 is inserted in a conventional CT scanner 104 and the scanner generates a 3D CT dataset 106 as is conventional. This CT dataset 106 is then supplied to a global predictive model 110. The global predictive model 110 preferably takes the form of a three-dimensional deep convolutional neural network, which acts essentially as a pattern recognizer, and is trained to recognize cancer in CT scan data in lung tissue. Such networks are described in the literature, e.g., Joao Carreira et al., Quo Vadis, Action Recognition? A New Model and the Kinetics Dataset, arXiv: 1705.07750 [cs.CV] (2017); Huang et al. paper cited previously at p. 1. The Carreira et al. and Huang et al. papers are incorporated by reference herein.

This model is trained to recognize cancer from a body of ground truth annotated CT scan datasets. In the present case, the National Lung Screening Trial (NLST) dataset was used for training. However, other datasets for training are mentioned in the literature and could be used, e.g., a Lung Image Database Consortium (LIDC) dataset mentioned in the Huang et al. paper, and the CT scan dataset used in the Kaggle's Data Science Bowl 2017 challenge, mentioned in the Stanford group's paper. In one embodiment, 3D inflated Inception V1 for the global model 110 is used because of efficient use of a graphics processing unit (gpu) memory. The Inception deep convolutional neural network architecture is described in the scientific literature. See the following references, the content of which is incorporated by reference herein: C. Szegedy et al., *Going Deeper with Convolutions*, arXiv:1409.4842 [cs.CV] (September 2014); C. Szegedy et al., *Rethinking the Inception Architecture for Computer Vision*, arXiv-1512.00567 [cs.CV] (December 2015); see also U.S. patent application of C. Szegedy et al., "*Processing Images Using Deep Neural Networks*", Ser. No. 14/839,452 filed Aug. 28, 2015.

This global model 110 is trained to predict at least the probability of the presence of cancer in lung tissue in the dataset 106 on a global basis. In one embodiment this global model 110 includes a lung segmentation feature to separate lung tissue from non-lung tissue in the CT dataset. The global model only predicts probabilities of cancer presence in the lung tissue. In one embodiment a mask R-CNN-based lung segmentation model is used to decide where to center crop the dataset to remove non-lung tissue, and only trained models for cancer detection in lung tissue are used instead of whole volume CT scan data. This procedure eliminates the anomalous possibilty of potential detection of cancer in non-lung tissue when our predictive models were only trained on ground truth annotated dataset for lung cancer (i.e., cancer in lung tissue).

The global model 110 was trained with several binary heads or classifiers (i.e., predictions to be made based on training data): Screening results on NLST, cancer outcome, and presence of >20 mm nodules. For example, the global model can be trained to predict probability of mortality within 5 years, and diagnosis of lung cancer within 2 years. The global model is also trained with 3D data augmentation, including random flipping along al axes and random shifts.

Additionally, the global model 110, as well as the second stage of the two-stage model, may include attribution mechanisms, such as Integrated Gradients, which basically Identify those portions/regions, i.e., location, of the dataset that contribute the most to the model predictions. These portions of the CT dataset can then be highlighted by adding bounding boxes in the images enclosing the cancer region identified from the attention mechanism, thereby allowing the user a tool for visualization of the cancer in the CT volume and giving the user confidence that the final prediction generated by the ensemble of models is trustworthy. The Integrated Gradients algorithm is described in the paper of M. Sundararajan et al., *Axiomatic Attribution for Deep Networks*, arXiv:1703.01365 [cs.LG] (June 2017), the entire content of which is incorporated by reference. The methodology will be described conceptually in the context of attribution of individual pixels in an image in a classification of the overall image. Basically, an Integrated Gradients score $IG_i$ (or attribution weight or value) for each pixel i in the image is calculated over a uniform scaling ($\alpha$) of the input image information content (spectrum of brightness in this example) from a baseline (zero information, every pixel black, α=0), to the full information in the input image (α=1), where IGi (score for each pixel) is given by equation (1)

$$IG_i(\text{image}) = \text{image}_i * \int_{c=1} \nabla F_i(\alpha * \text{image}) d\alpha \qquad (1)$$

where F is a prediction function for the label;
$\text{image}_i$ is the value of the ith pixel;
$IG_i$ (image) is the integrated gradient w.r.t. the $i_{th}$ pixel, i.e., attribution for $i_{th}$ pixel; and
$\nabla$ is the gradients operator with respect to $\text{image}_i$.

Section 3 of the Sundararajan at al, paper explain the algorithm further and that description is incorporated by reference. The adaptation of that technique to a 3D volume as in a CT scan is considered within the ability of persons skilled in the art.

The use of attention mechanisms in deep learning neural networks is described in the conference presentation of D. Bahdanau et al., *Neural Machine Translation by Jointly Looming to Align and Translate*. January 2014 (arXiv: 1409.0473[cs.CL]. Further explanations of attention mechanisms in the context of healthcare include Choi et al., *GRAM: Graph-based attention model for Healthcare Representation Learning*, arXiv:1611.07012v3 [cs.LG] April 2017 and Choi at al., *RETAIN: an Interpretable Predictive Model for Healthcare using Reverse Time Attention Mechanism*, arXiv:1608.05745v3[cs.GL] February 2017.

As explained previously, the global prediction model 110 generates a prediction, Pg, which reflects the probability of the presence of cancer in lung tissue in the CT dataset on a global basis. The location of the possible cancer is also identified, e.g., through the use of an attention mechanism such as Integrated Gradients. Data reflecting this cancer probability 112 and location is stored in memory, such as the memory 120 of a computer system 122 implementing the method of FIG. 1.

The CT dataset 106 is also provided to a two stage prediction model consisting of a first stage detection model 130 and a second stage probability model 132. The first stage detection model 130, which may also take the form of a 3D deep CNN, identifies one or more cancer detection candidates 134 (three of which are shown in FIG. 1) and generates cropped 3D volumes for each of the candidates, for example 45 mm³ or 90 mm³ volumes enclosing the possible cancer. The cropped 3D volumes could also be used to highlight the location of the detected cancer as an alternative to attention mechanisms such as Integrated Gradients. Our detection model is based on the detection model architecture described in the following paper, but generalized to three dimensions: Tsung-Yo Lin et al., *Focal Loss for Dense Object Detection*, arXiv-1708.02002 [cs.CV] (August 2017). This model is similar to RetinaNet with a focal loss single stage detector, but fully 3D convolutional and with target assignment. For training this model, bounding boxes for all cancer positives and their priors in the NLST dataset are collected. Patch-based training of this model is used, but whole volume inference to generate the detection candidates. The detection model uses the same base feature extractor as the global model 110. In one embodiment, the detection model is also pre-trained on a nodule detection task on a different dataset (LIDC) but only nodules are labeled in that set and it is not known whether a nodule is cancer or not.

These detection candidates 134 of FIG. 1 are then fed into the second stage probability model 132, also taking the form of a deep CNN generalized to three dimensions in one embodiment, which then generates a cancer probability prediction p for each of the candidates. This model is also trained with focal loss (see the Un at al, paper cited above). Detection candidates are randomly sampled at train time based on detection probability. For 90 mm³ patches, predictions at various feature layers are made separately and combined as if they were separate detection candidates (see FIG. 3 and the description below). This model also begins training from the weights of the detection model 130.

For example, and referring to FIG. 1 again, if there are three candidates 134 (1, 2, 3) the second stage model 132 generates a set of probabilities [p1, p2, p3], one for each candidate.

As noted previously, the system optionally and preferably includes multiple second stage models, 132A, 132B, 132C . . . . Each second stage model 132A, 132B, 132C, etc. uses a different set of parameters for making the probability predictions p for the detection candidates. Possible differences in parameters include 1) different patch sizes (i.e., different volumes of cropped 3D data in the dataset) generated by the detection model, e.g. 45 mm³ and 90 mm³ volumes, 2) different optimization parameters used during learning, such as the learning rate, 3) taking models at multiple points during the course of training (weights change over the course of training so each model would have slightly different predictions); 4) different parameters as a result of data augmentation during training, and 5) different model architectural settings, such as the depth, kernel size and number of convolutions for each model. As an example of 4), in one implementation the training data is randomly altered during training of the second stage probability models 132 in order to expose the models to more variation. For example, in one embodiment small random rotations of the input volumes are generated. This data augmentation has parameters which can be varied among members of the ensemble (132A, 132B . . . ), for example the amount of random rotation. As an example of 5), the different second stage probability models are each deep convolutional neural networks but each one has a different model architecture, for example the models vary as to the depth, kernel size and/or the number of convolutions.

So, while in practice there are three such second stage probability models 132 shown in FIG. 1, the number of such models which may be used in practice may vary and could be say 2, 4, 5, 6, 10 or more, and the model parameters for each one vary in accordance with the discussion in the preceding paragraph.

Figure 2:
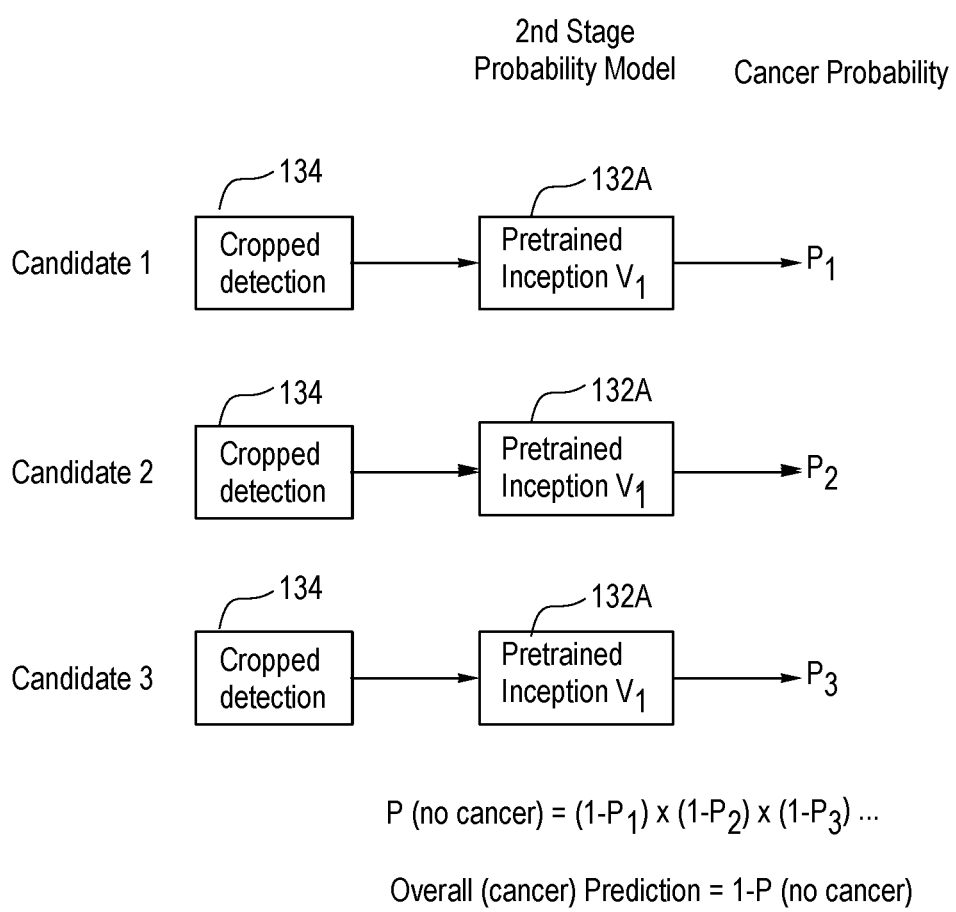
FIG. 2 is an illustration of the generation of a cancer probability prediction by a second stage probability model of FIG. 1 and an overall cancer prediction for a set of candidates 1, 2, 3 by a single second stage model. The procedure of FIG. 2 is repeated for each of the second stage models if the system includes more than one second stage model.

FIG. 2 is an illustration of the generation of a cancer probability prediction by a second stage probability model of FIG. 1 and an overall cancer prediction for a set of candidates 1, 2, 3 by a single probability model 132. The procedure of FIG. 2 is repeated for each of the second stage models if the system includes more than one second stage model. Candidate 1 in the form of a cropped 3D volume is applied to the second stage probability model 132 and a cancer probability prediction p1 is generated. Similarly, Candidate 2 in the form of a cropped 3D volume is applied to the second stage probability model 132 and a cancer probability prediction p2 is generated. This process is repeated for each of the candidates, three of which are shown in the example of FIG. 1. A probability for no cancer P (no cancer) is computed according to equation 2:

$$P(\text{no cancer}) = (1 - p1) \times (1 - p2) \times (1 - p3) \qquad (2)$$

The overall cancer prediction from the model is then given by equation 3:

$$P(\text{cancer}) = 1 - P(\text{no cancer}). \qquad (3)$$

The same calculations are made for each of the second stage models 132B, 132C, etc. if present in the system.

Referring again to FIG. 1, an ensemble prediction $P_E$ which is an overall or ensemble prediction of the presence of cancer in the CT dataset 106 is then computed as a function $f$ of the prediction of the global predictive model $P_G$, and the set of predictions [p1, p2, p3]$_A$, [p1, p2, p3]$_B$, etc. produced by the second stage models 132A, 132B etc. In one embodiment the set of predictions [p1, p2, p3]$_A$, [p1, p2, p3]B . . . are converted to P(cancer) as per equations (2) and (3), which can be written as $P_A$, $P_B$, . . . and $f$ is then an averaging calculation. For example, if there are three second stage models, $P_E$ is given by equation (4)

$$P_E = (P_G + P_A + P_B + P_C)/4 \quad (4)$$

where $P_G$ is the global model probability prediction, e.g., on a percentage scale of 0-100.

Figure 4:
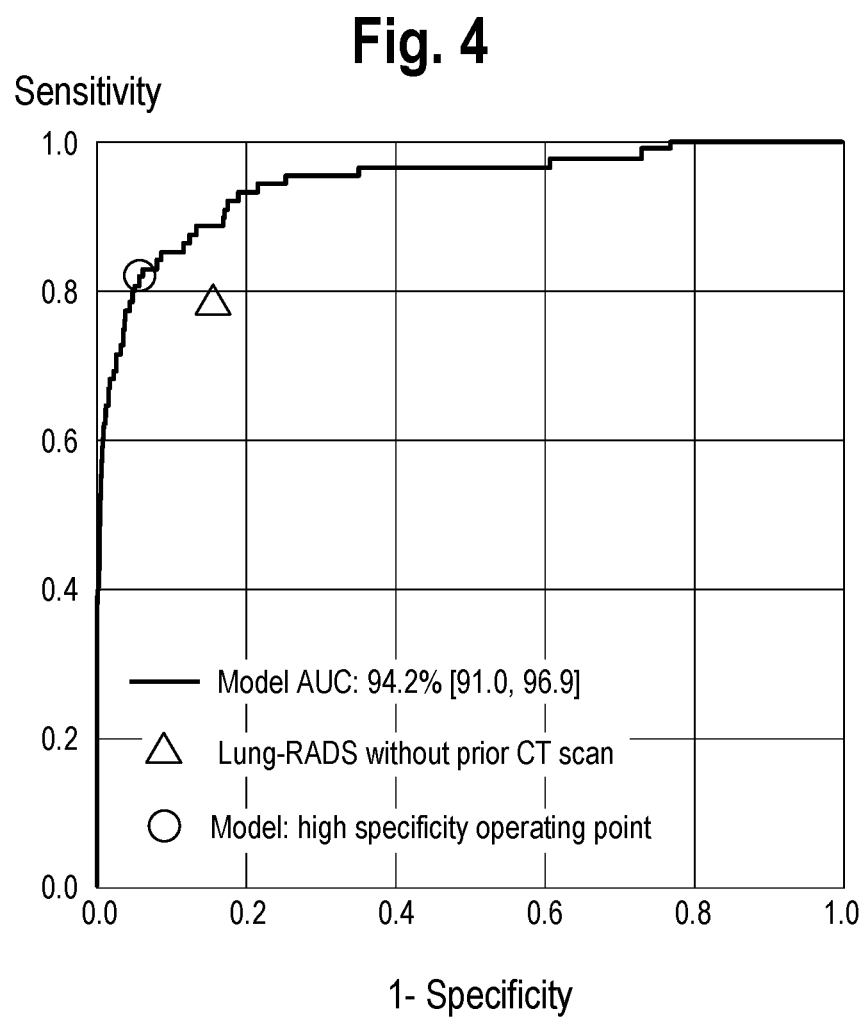
FIG. 4 is a receiver operating characteristic area under the curve (AUC) plot showing performance of the system of FIG. 1 relative to retrospective comparison of Lung-RADS™ criteria by trained readers to the NLST dataset.

Experimentation on the contributions of the various models to arrive at the ensemble probability $P_E$ may dictate other possible solutions besides an averaging calculation, such as by providing different weights to the one or more second stage models, or by weighting the global model prediction $P_G$ more or less than the same as the predictions $P_A$, $P_E$, . . . of the second stage models. As another example, an averaging could be performed of the second stage model predictions $P_A$, $P_B$, . . . and then this average is then averaged (either directly or with weighting) with the global probability $P_G$. Investigation of receiver operator characteristic (ROC) AUC plots such as shown in FIG. 4 for different functions $f$ can be used determine an optimal function $f$ to combine the global and second stage model predictions.

Additionally, in a configuration where the global model is a neural network, e.g., deep neural network with many different layers (e.g. convolutional layers, fully connected layers, attention mechanisms, etc.), the final step that generates cancer prediction probability is the last layer (with just one output). Intermediate convolutional layers (e.g. the penultimate layer) tend to contain very rich information, often more than the final prediction, which is just one number. These hidden, intermediate units or layers produce an output (referred to as "feature maps", i.e., the features and their location) which can be appended with the feature maps of an intermediate layer of the second stage model(s) (also deep convolutional neural networks), to train an improved final layer/classifier in the global model. This represents still another way of combining the second stage model(s) with the global model to generate a final or ensemble probability prediction of cancer.

Additionally, it is possible to append the feature maps in the opposite direction. That is, the feature maps from an intermediate layer in the global model can be concatenated to the feature maps of an intermediate layer in a second stage model, and the final predictions are generated from the second stage model, as depicted in FIG. 5. Accordingly, appending feature maps in either direction is possible, and also in both directions are also possible, i.e., feature maps from an intermediate layer in the global model are concatenated to feature maps at an intermediate layer in the second stage model, and feature maps from an intermediate layer in the second stage model are concatenated to feature maps in an intermediate layer of the global model. For example, in development of the global model and second stage models, one can continue to fine-tune the second stage model and its layers, but freeze the global model features. The other direction is possible, wherein the second stage model is frozen and one can continue to fine-tune the global model with appending the feature maps from the second stage model to the global model. Once the models are fully developed and frozen, then one can perform the appending of the feature maps in either direction or in both directions to generate the ensemble probability as explained above.

It is then possible to propose alternatives to the existing Lung-RADS™ risk stratification buckets based on probability prediction of the ensemble of models as explained above. For example, one can set cutoffs on this final probability in order to place the CT scan cancer predictions into a risk bucket. As an example using hypothetical probability cutoffs, if $0 < P_E < 0.1$, that would be the first risk bucket. If $0.1 < P_E < 0.2$ that would be the second bucket and so on. It is possible to make buckets that are similar to the risk buckets existing in Lung-RADS™ today by determining the appropriate cutoffs for our probability predictions. Such cutoffs could be ascertained by applying the methodology of generating ensemble probabilities retroactively to a given dataset (e.g., the NLST dataset) and studying the clinical data associated with patients in each grouping of a proposed cutoff schema, and adjusting the cutoffs until the clinical data in the patients in the groupings match or approximate existing, known groupings such as Lung-RADS™, or any new grouping schema that may be designed. We propose to replicate a previously existing approach to estimate the PPV of Lung-RADS 3+, Lung-RADS 4A+, and Lung-RADS 4B/X. We then chose operating points that matched these PPV values on our tune set, in order to compare with the three existing risk buckets. These operating points are noted as "gRADS" scores of 3+, 4a+, and 4b/x, designed to correlate with Lung-RADS cut-offs for malignancy-positive with the same Lung-RADS scores.

Figure 3:
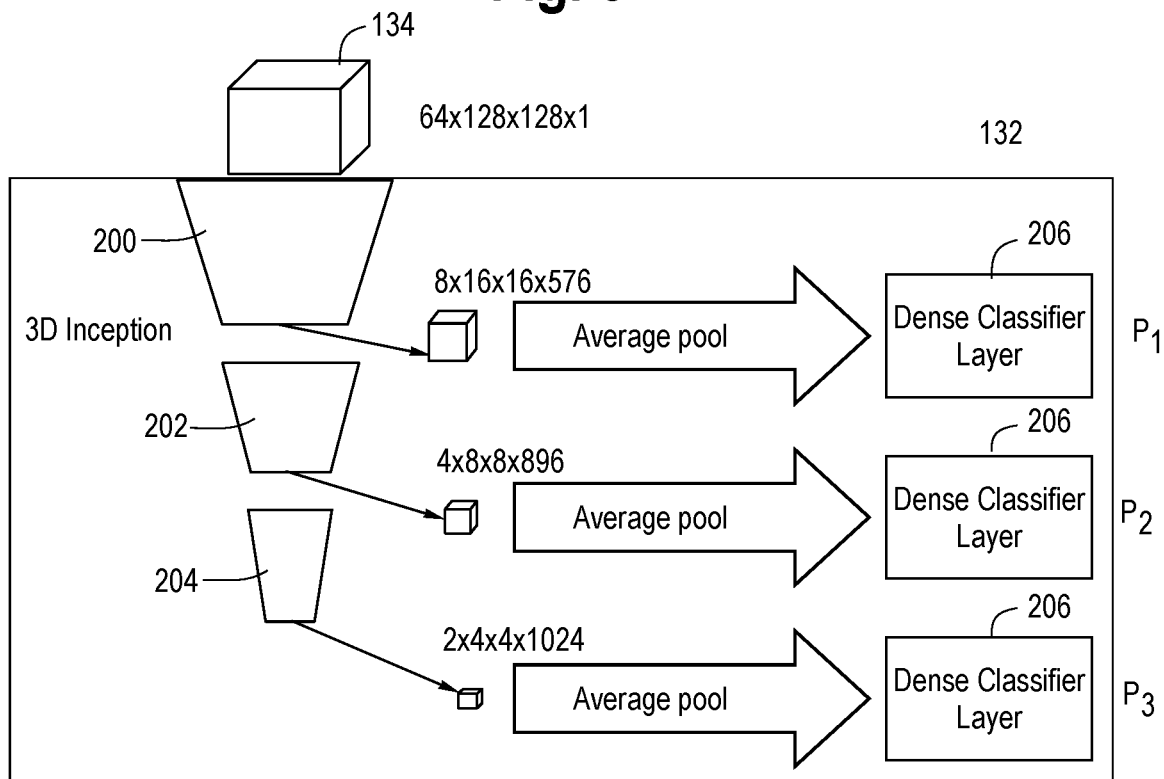

FIG. 3 is an illustration of a multi-scale feature extraction method of generating feature maps and then predictions p1, p2, p3 for a given input cancer candidate 3D volume 134 by a single second stage model 132. The model 132 consists of a 3D Inception deep convolutional neural network includes layers 200, 202, 204. The average pool layer down-samples by averaging rectangular regions of the input. The average pool generates a vector of a multitude of features for classification (such as 576 features) which are provided to a dense classification layer 206 which generates a classification in the form of prediction p1. The other layers 202 and 204 in the 3D Inception model generate additional volumes and respective classification features and the dense classification layer generates classification predictions p2 and p3. Hence, in this example a single cancer detection candidate fed into the second stage model produces three different cancer probability predictions, p1, p2 and p3.

FIG. 4 shows a plot of the performance of our ensemble method as a receiver operating characteristic (ROC) AUC curve. FIG. 4 plots the Sensitivity and Specificity of the proposed method. A high-specificity operating point is shown along with a comparison to human readers using Lung-RADS™ without priors. The area under the receiver operator curve of the deep learning model was 94.2% (95% Confidence Interval (CI) 91.0, 96.9). Compared to radiologists using Lung-RADS™ on the test set, the trained model achieved a statistically significant absolute 9.2% (95% CI 8.4, 10.1) higher specificity and trended a 3.4% (95% CI −5.2, 12.6) higher sensitivity (not statistically significant). Radiologists qualitatively reviewed disagreements between the model and Lung-RADS™. Preliminary analysis suggests that the model may be superior in distinguishing scarring from early malignancy.

Accordingly, this disclosure presents an improved deep learning approach to lung cancer detection and weening. The ensemble of models can potentially help reduce unnecessary invasive procedures (e.g., biopsy, surgery) by helping radiologists avoid false positives in CT scan datasets.

II. Ensemble of Deep Learning Models with Current and Longitudinal Image Datasets, and/or Multimodal Image Datasets As noted above in the background section of this document, longitudinal image datasets (i.e., prior patient image datasets available for comparison to the current or most recent image dataset), and multimodal image datasets, can help improve cancer screening diagnosis or cancer detection in diagnostic images. Often, interpretation of such datasets is manually or semi-automatically performed by radiologists comparing the same region of the image across multiple times. Automated approaches using deep learning can offer the ability to identify subtle cues across multiple images to identify and classify cancer. We present in this section of this document a general approach for incorporating longitudinal or multimodal imaging for the purposes of cancer detection and classification using an ensemble of deep learning models.

In the following description, the topic of lung cancer screening from low-dose (LD) chest computed tomography (CT) images is presented by way of example which includes current and prior image datasets. However, the approach described can generalize to other cancer topics and radiology imaging modalities, such as for example longitudinal magnetic resonance Imaging (MRI) datasets for prostate cancer detection and classification.

The ensemble of deep learning models includes a global model in the form of a 3D convolutional neural network (CNN), for example using a 30 Inception architecture, which extracts features in the datasets indicative of the presence of cancer on a global basis. This global model can be trained to predict, on a global basis (e.g., over an entire CT volume where the medical image dataset consists of a 3D volumetric image dataset), the probability of presence and location of cancer in the medical image-based dataset and identify or extract features which are associated with this prediction. The global predictive model uses as input a recent and, and optionally, longitudinal image datasets. The global model may therefore take as input the entire volume dataset (e.g., a recent one, and optionally longitudinal datasets) and extracts features indicative of the presence of cancer. Optionally, in an example of a CT dataset for lung cancer, this global model includes a feature to isolate lung tissue from non-lung tissue in a chest CT dataset and extracts a set of features indicative of the presence of cancer in just the lung tissue.

The ensemble of deep learning models also includes a two-stage prediction model which receives as input the recent and longitudinal image datasets. This two-stage prediction model includes a first stage or detection model and a second stage or probability model. The detection model operates on the full volume of the current CT dataset and identifies cancer detection candidates (for example, in a CT dataset, different cropped volumes of 3D data in the CT dataset containing candidates which may be cancer, not just merely nodules, which may or may not be cancerous). The cancer detection candidate volumes are then located in the prior full volume dataset via a registration or relative landmark positioning procedure. Each of the cancer detection candidate volumes are passed through the second stage model which includes a 3D feature extractor, e.g., a deep convolutional neural network such as 3D Inception architecture, as used in the global model.

All of the features from the feature extractor for each of the cancer detection candidates ("feature maps" in this document) are concatenated after average pooling and/or operation on convolutional layers. These features are also concatenated with the features (feature map) extracted from the global model. After such concatenation, the second stage or probability model performs a classification operation (e.g., by operation of one or more fully connected layers in the neural network architecture) which assigns a cancer probability p to each of the cancer detection candidates. In other words, the features which are extracted from the global model are concatenated with the features for each cancer detection candidate patch from the second-stage model, so that all predictions rely on both the nodule-level location information (from the 1st stage of the two stage model) as well the global context from the global model. The predictions for each cancer detection candidate can be combined into a single malignancy score for the imaging datasets, for example, computed based on a noisy-or approach as described below. In brief, the prediction from each cancer detection candidate is interpreted as the probability of malignancy for that candidate, and the final prediction (on the entire volume) is the probability that at least one of these ROIs is malignant, as will be explained below. This final probability prediction is referred to below as a "malignancy score."

Given the malignancy score, the region or location in the volume which is the probable location of cancer can be highlighted by taking the sub-volume from the first stage or detection model of the two-stage model that caused the highest score. Within the sub-volume, attribution methods, also known in the art as "attention mechanisms", such as Integrated gradients, can be used to identify the location more precisely. Additionally, attribution methods on the global model can be used to identify multiple regions in the image that lead to the cancer prediction. This may include abnormal lymph nodes or even vascular tissue around a cancerous nodule.

In one possible configuration, there may be more than one, such as three, five, or even ten different second stage probability models, e.g., models A, B, C, D, etc., each with its own set of parameters, and each making a prediction of the probability of cancer in each of the detection candidates using both the recent and prior image datasets and the features extracted from the global and detection models. Possible differences in parameters which define such second stage models include 1) different patch sizes (i.e., varying size volumes of cropped 3D data in the dataset, in order to detect cancer at different scales), 2) different optimization parameters used during learning, such as learning rate, 3) taking models at multiple points during the course of training (weights change over the course of training so each model would have slightly different predictions); 4) different parameters as a result of data augmentation during training, and 5) different model architectural settings, such as the depth, kernel size and number of convolutions for each model. In particular, in one implementation the training data may be modified to generate additional training data during training in order to expose the model to more variation. For example, small random rotations may be applied to the input volumes to generate additional training volumes. This data augmentation has parameters which may vary among members of the ensemble, for example the amount of random rotation.

The prediction probability generated by the second stage probability models can be combined, for example, in accordance with some defined function $f$, or algorithm, to generate an overall or final probability prediction (e.g., a "malignancy score," typically presented in terms of percentage from 0 to 100) of cancer/no cancer in the medical image-based dataset and location of the possible cancer. In one configuration, these probabilities can also be used in a novel scoring method, either to approximate existing scoring schemas or by defining a new one. The defined function $f$ could consist of an averaging of the predicted probabilities of each of second stage models, i.e., computed over all the cancer detection candidates, or in the form of a weighted average.

FIG. 5 illustrates our system and method deep learning based classification of cancer with longitudinal imaging. The reader will note the general similarity to the system described above in FIG. 1, but it has a few differences: it includes additional capabilities to use as inputs the longitudinal image datasets, and the global model is not used for prediction per se but rather to extract features (i.e., feature map) in the datasets which are indicative of the presence of cancer and such features are appended or concatenated to the extracted features of the second stage probability model to generate a prediction of probability of cancer in one or more detected cancer candidates.

Our approach, at a high-level, consists of a two-stage model 502 including a first stage or detection model 502A for cancerous nodule detection on 3D CT patches, including a current CT volume 520 and a longitudinal or prior CT volume 522, followed by malignancy prediction on the top detected regions of interest (ROI) by a second stage or probability model 502B. In addition, the system includes an end-to-end global convolutional model 500 operating on the entire volume, using current CT volume 504 and optionally a prior CT volume 506, respectively, to extract features in the dataset indicative of cancer on a global basis. The use of prior CT volume 508 may give slight improvement in the performance of the models and is considered optional and not necessary. Features from the global model are appended to features extracted from the second-stage model, so that all predictions (generated by a classifier indicated at 538) rely on both nodule-level local information as well as global context. The output 540 is the probability prediction of cancer for the patient given the current and prior CT image datasets, using an algorithm or function such as the Noisy-or approach described below.

The optionally resampled full volumes of the current and longitudinal image are passed through a 3D feature extractor (508), e.g. 3D Inception deep CNN, of the global model 500 to capture a global context. The features are represented as 8×8×8 smaller volumes (510) with 1,024 feature channels. These features are concatenated in the channel dimension as Illustrated in the upper portion of the FIG. 5 and combined as indicated at 514 in convolutional layers and an average pool of five hundred and twelve features. The feature map is then concatenated as indicated at 536 with a feature map from the second stage probability model.

The two-stage model 502 receives as input the full volume current high resolution CT dataset 520 and a prior full volume high resolution CT dataset 522, The two-stage model includes a first stage or detection model 502A in the form of a nodule detector 524 which is trained to detect cancer candidates, not merely nodules per se. One of these cancer candidates (sub-volumes) is shown at 528. Using a registration or relative landmark positioning procedure this smaller sub-volume or ROI is also identified in the prior full volume CT dataset 522, shown at 526. Alternatively, the nodule detector 524 can operate on the prior full volume CT dataset to identify the corresponding ROI 526. Each sub-volume or ROI 526, 528 passes to a second stage probability model which includes a 3D feature extractor (530), e.g. 3D Inception deep convolutional neural network. The 3D feature extractors 530 use shared weights i.e., weights indicating how to process the features; these weights need not be the same as the weights of the 3D feature extractor 508 of the global model. The small volumes 532 represent a compressed volume (1×2×2) of 1,024 feature channels. These volumes are concatenated in the channel dimension as indicated in FIG. 5 and subject to average pooling and/or convolutional layers as indicated at 534 to result in five hundred and twelve features. This feature map resulting from 534 is concatenated with the feature map of five hundred and twelve features from the global model at 536 and then the combined 1,024 features are subject to a classification operation as indicated 538 (e.g., the output of fully connected layers in the second stage probability model 502B). This classification step is the generation of a probability prediction for each of the ROI's identified by the nodule detection or first stage model 524. As an output 540, a single malignancy score is computed based on the noisy-or approach. Note that the number of sub-volumes or ROIs can vary depending upon the application and requirements. Also, in the case where prior imaging is not available, a blank image can be fed through the network. This is possible as long as the models are trained to accept blank images.

The predictions from each ROI are combined into a single malignancy score in an output step (540) on the entire volume using the noisy-or approach: the prediction from each ROI is interpreted as the probability of malignancy for that ROI, and the final prediction (on the entire volume) is the probability that at least one of these ROIs is malignant:

$$P[\text{overall malignancy}] = 1 - \prod_{ROIs}(1 - P[ROI \text{ malignancy}])$$

where P[ROI malignancy] is predication generated by the classification process (538) for the given ROI. This is similar to the explanation for generation of a probability prediction for the system without priors, in FIG. 1 as explained above.

It will be appreciated that the system described above in FIG. 5 is applicable to different types of 3D volumetric datasets, such as MRI, PET or CT scan which have prior or longitudinal and current image datasets. It will also be appreciated that the system of FIG. 5 is also applicable to the situation where Instead of current and longitudinal datasets you have multimodal datasets in which instead of a "prior" volume e.g., CT volume 522 in FIG. 5, you have for example as input a different type of 3D volume dataset, such as CT and MRI dataset pair, or a CT and PET dataset pair, or a MRI, CT and PET dataset triplet, or a set of MRI images which are obtained in single MRI scanning operation, e.g., by controlling the scanner's settings to obtain different types of MRI images, e.g., sometimes known in the art as a multimodal MRI image dataset.

Figure 6:
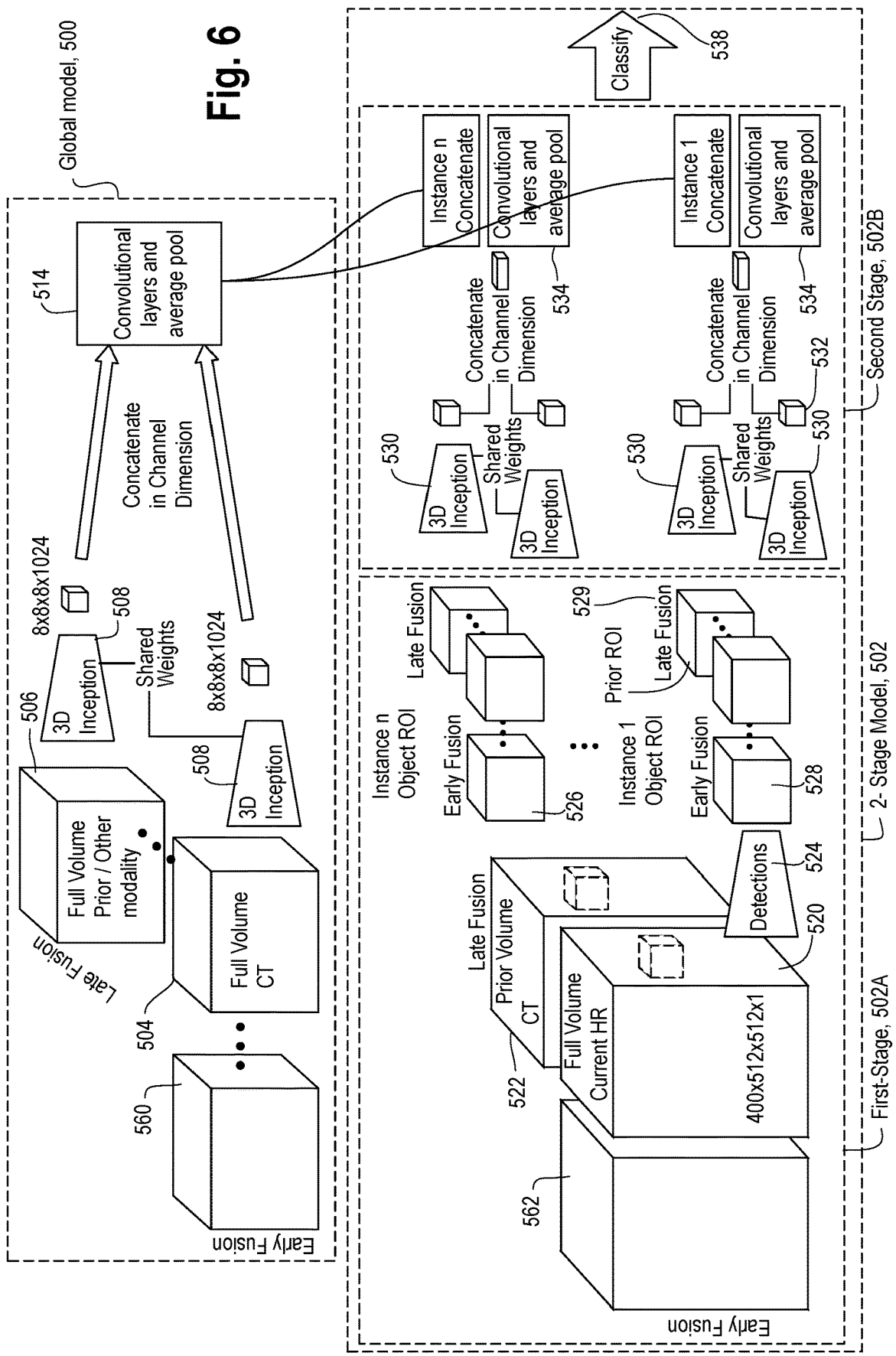
FIG. 6 is an illustration of a generalized deep learning system for incorporating longitudinal or multimodal images for performing detection and classification of medical image-based datasets.

A generalized illustration of the deep learning system of taking into account prior or other modality image datasets Is shown in FIG. 6. As indicated at 562 and 560 there is preferably performed an initial fusion or registration step so as to bring all the image datasets into a common 3D coordinate system such that the images overlap or are in registration. The degree of accuracy of the registration or fusion is not particularly critical.

Then, the global model 500 proceeds to operate on the full volume Image datasets with feature extractors 508 (e.g., 3D Inception architecture deep convolutional neural networks) to extract features which are indicative of the presence of cancer in the full volumes on a global basis. These features are concatenated in the channel dimension and subject to convolutional layers and average pooling at 514. The use of prior or other modality images (508) in the global model is again considered optional and not essential; the use of prior or other modality images may improve overall model performance slightly.

Simultaneously, one of the full volume datasets 520, 522 is subject to a 3D detection model 524 which identifies a sub-volume (sub-volume 1) which is a cancer detection candidate 528, and using the results of the early fusion process the corresponding sub-volume or ROI 526 is identified in the other volumes 522. In this example, there are n cancer detection candidates identified by the detection model 524, where n is some integer greater than or equal to 1, typically say 2, 3 or 5. Accordingly there are n ROIs. Each of the n sub-volumes or ROIs are subject to a 3D feature extractor 530 (deep convolutional neural network such as an 3D Inception) which generates a compressed volume with 1,024 features in the channel dimension.

For each of these n ROIs, these volumes are concatenated in the channel dimension. After processing by additional convolutional layers and average pooling (534), each instance is then concatenated by the feature maps from of the global model, and then subject to a classification operation as indicated at 538, resulting in a probability prediction for each of the n ROIs. These probability predictions are then combined using the Noisy-Or approach described above.

It will be appreciated that the description of FIGS. 5 and 6 has used a single second stage probability model 502B. However, it is possible to use multiple second stage probability models, as explained in the description of Section 1, in which each of the second stage probability models has slightly different model parameters, and the results of the second stage probability models are then combined or averaged among all the models, in accordance with some function $f$, and then after averaging the final probability is generated in accordance with the Noisy-Or approach.

Figure 7B:
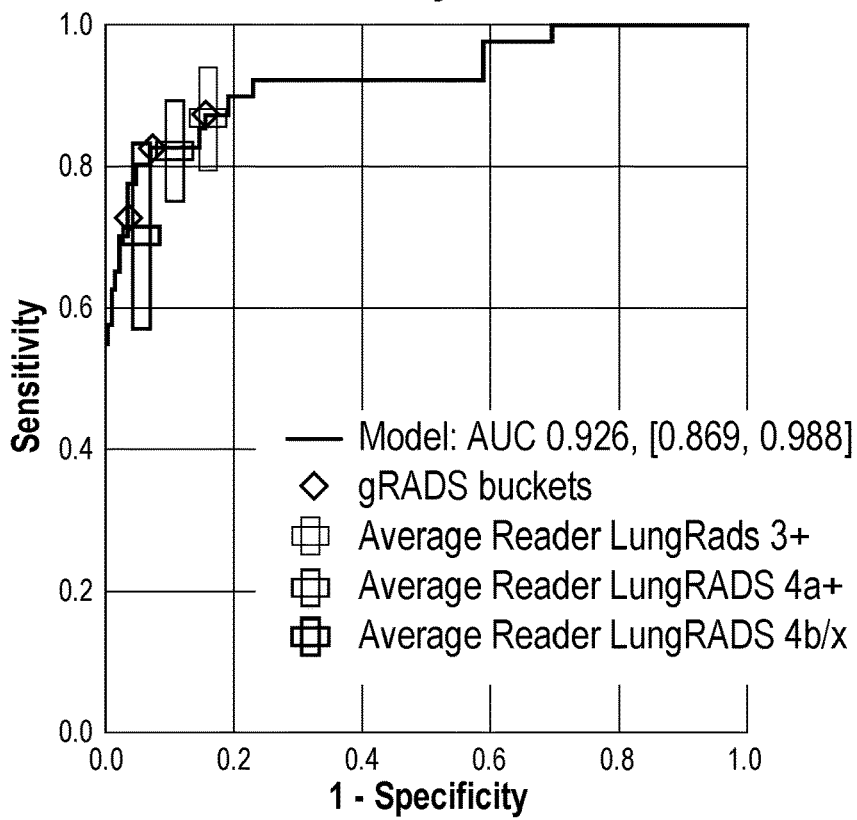
Figure 7C:
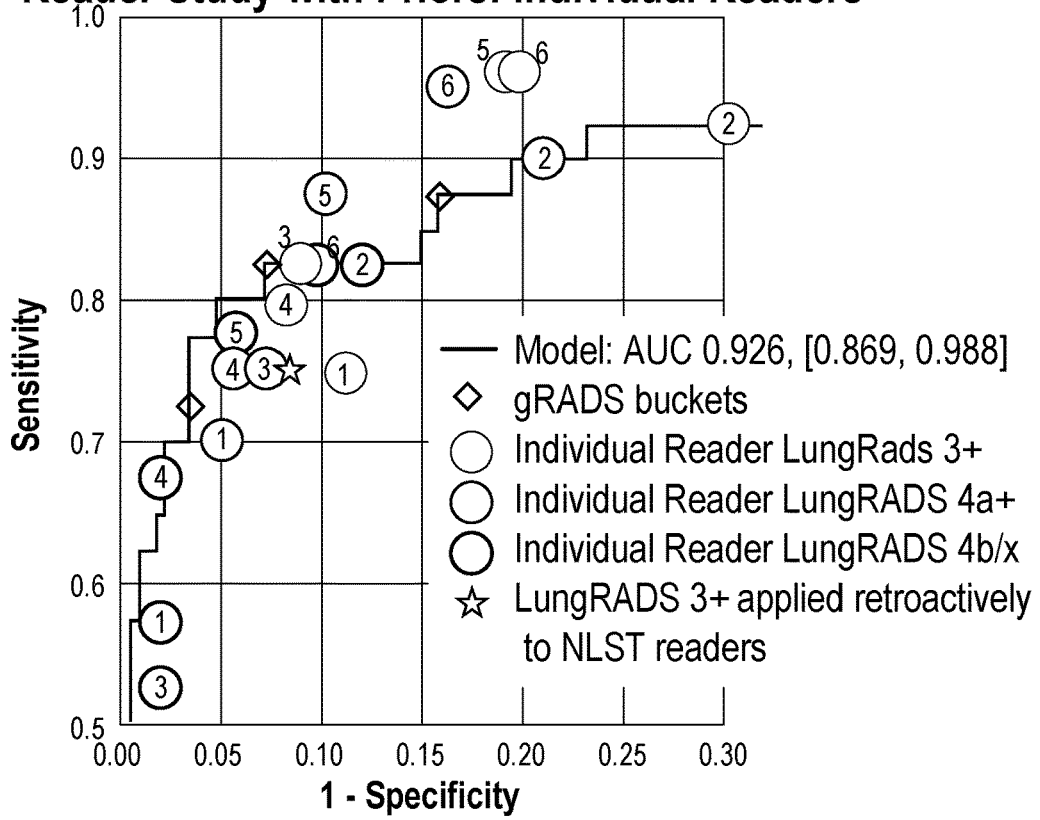

FIG. 7A-7C are receiver operating characteristic area under the curve (AUC) plots showing performance of the system of FIG. 5 with and without current and longitudinal image datasets, relative to retrospective comparison of Lung-RADS™ criteria by trained readers to the NLST dataset.

FIGS. 8A-8C are longitudinal CT scan images of a patient with a bounding box 800 defining a region of interest identified by the first stage or detection model of the two stage model as being potentially cancerous.

FIGS. 9A-9C is another example of three different CT scan images of a patient with a box 902 showing a region of interest identified by the first stage or detection model of the two stage model as being potentially cancerous. The larger bounding box 900 is available for the prediction module of the second stage model to make a prediction of probability of cancer and to provide surrounding contextual information.

FIGS. 10A and 10B illustrate an example of a registration of a prior and current CT scan image based on the center of an identified ROI.

Figure 11A:
FIG. 11A-11C show the results of the attribution regions derived from the second stage probability model.
Figure 11B:
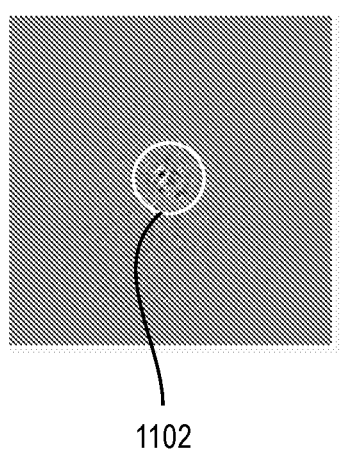
Figure 11C:
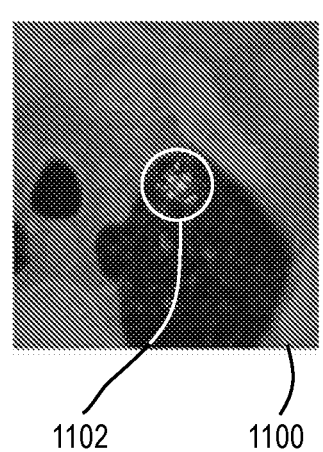

FIGS. 11A-11C show an example of the use of an attention mechanism such as integrated gradients in the second stage model. In FIG. 11A, there is a shown a portion of a CT scan image 1100 which shows a region of interest which was predicted to be likely cancerous. FIG. 11B shows the results of the application of the attention mechanism to the image 1100 of FIG. 11A, namely a small region 1102 which is illustrated in a contrasting color to indicate the specific region of the image 1100 which contributed the most to the prediction of likely cancer. In FIG. 11C, the image 1100 is again rendered but with the superposition of the attention mechanism results 1102 of FIG. 11B. In simple terms, the radiologist investigating the image of FIG. 11C is directed to the portion of the image (1102) that is most responsible for the prediction of cancer as a result of the use of the attention mechanism.

Further Considerations

The system of FIG. 1 could be deployed in a cloud environment in which the global and two stage predictive models are implemented remotely (e.g., in the cloud. e.g., by a service provider that trained and developed the models). In this configuration, a CT scan dataset is sent over a computer network (e.g., the Internet) and the service provider returns a final probability score and location to a clinic or office where the CT dataset is obtained, where a radiologist is considering the CT scan, or where a physician may be consulting with a patient in regards to a CT scan obtained from the patient and planning further treatment. Alternatively, the system of FIG. 1 could be implemented locally, i.e., with the computing resources and deep learning models located locally to the office, clinic, or hospital where the CT dataset is obtained, or viewed on a workstation e.g. by a radiologist or a primary care physician.

III. Predicting Brain Age Using Structural Neuroimaging and Deep Learning

This section will describe the use of the proposed deep learning models for brain-age prediction from structural magnetic resonance imaging data sets.

Age-related disease and disability impose a growing burden on society. Since aging effects are subject-specific, markers of the underlying biological aging process are needed to identify people at increased risk of age-related physical and cognitive impairments. Structural MRI images are extremely useful in measuring age-related changes in the brain. Thus, the goals of this study are to develop a brain-age-predicting algorithm based on SMRI images and to investigate the predicted brain age as a biomarker of aging-related diseases in the brain Early detection of aging-related diseases requires a model of the underlying biological aging process. In this section, we describe a brain-age predictor by using structural magnetic resonance imaging (SMRI) and deep learning and evaluate the predicted brain age as a marker of brain-aging. Our approach does not require domain knowledge in that it uses a transfer-learning paradigm and has been trained and validated on real SMRI data collected from elderly subjects. We developed two different predictive models based on the proposed convolutional neural network (CNN) with regression and bucket classification to predict brain ages from SMRI images. The regression and classification-based models achieved root mean squared errors (RMSE) of 5.54 and 6.44 (years), respectively, in predicting brain ages of cognitively normal subjects. Further analysis showed that there is a substantial difference between the predicted brain ages of cognitively impaired subjects and normal subjects within the same chronological age group.

The models described in this section correspond generally to the "global model" 110 of FIG. 1 and the global model 500 of FIG. 5; in the work described below we did not use the two-stage models of FIG. 1 and FIG. 5.

The major differences between our approach and previous efforts on this subject are, 1) our use of deep-learning to learn relevant features from raw SMRI images without requiring domain knowledge, and 2) our validation of the proposed approach with data collected from subjects at risk of developing Alzheimer's disease, a major aging-related disease. Prior studies have proposed machine-learningbased approaches that use a Gaussian process regression to predict brain age from SMRI images. See J. H. Cole, et al., "Predicting brain age with deep learning from raw imaging data results in a reliable and heritable biomarcer," Neuro-Image, vol. 163, pp. 115-124, 2017; J. H. Cole, et al., "Brain age predicts mortality," Molecular Psychiatry, 2017. However, those approaches have relied on features derived from domain knowledge of the structure of the human brain. On the other hand, P. Sturmfels, et al., "*A domain guided CNN architecture for predicting age from structural brain images*," arXiv preprint arXiv:1808.04362, 2018, proposed a CNN-based architecture that uses minimal domain information to predict brain age. However, that study was performed using SMRI imaging data collected from children and it is unclear whether it can predict aging-related disease-risk of elderly patients.

We employed a transfer-learning approach based on a pre-trained 3D inception-V1 feature extractor and retrained to predict brain age from SMRI images as regression and classification problems. This model, analogous to the "global model" described in previous sections of this document, did not require any domain knowledge and predicted brain ages in two different ways, 1) using a regressor, and 2) using a bucketed classifier (described below). We evaluated our approach using the Alzheimer's disease neuroimaging initiative (ADNI) dataset. Regression and bucketed classifier methods achieved root mean squared errors (RMSEs) of 5.54 and 6.44 (years), respectively, in predicting brain age of cognitively normal subjects. In addition, further analysis showed that the predicted brain ages of cognitively impaired subjects are on average 3.24±2.12 and 2.67±2.36 years higher than their chronological ages when regression and bucketed-classification approaches, respectively, are utilized. In essence, our approach utilizes a CNN-based model for predicting brain age based on SMRI images without using any domain knowledge and demonstrates that brain ages predicted by using our approach can be used to identify aging-related disease risk.

Methodology

Figure 12:
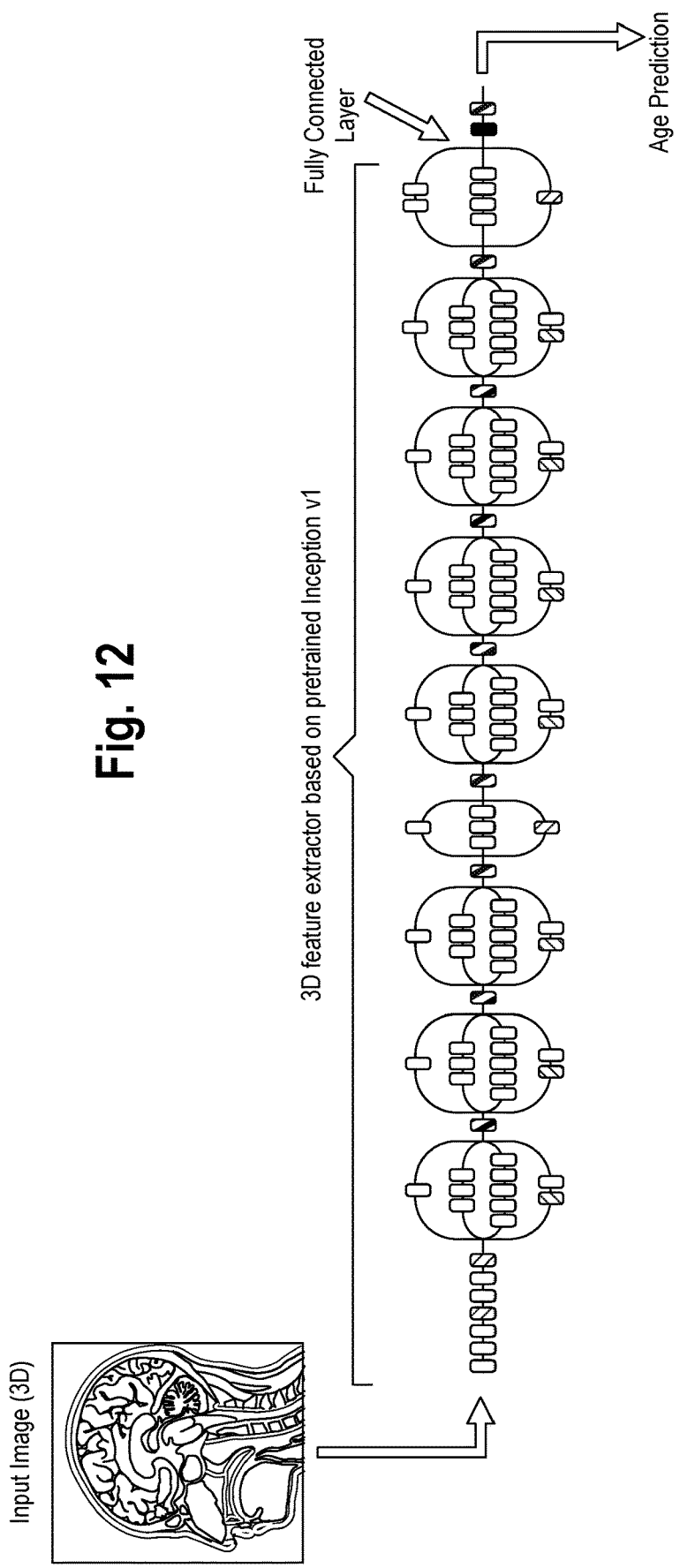
FIG. 12 is diagram showing a deep learning model for predicting brain age from 3D Structural Magnetic Resonance Imaging (SMRI) images of the brain without requiring any domain knowledge. Two variations of the model of FIG. 12 are described below which predicted brain ages in two different ways: 1) using a regressor, and 2) using a bucketed classifier.

The overall flow of our approach is shown in FIG. 12. This model of FIG. 12 is indicated in the upper portion of FIG. 5, the global model. 3D SMRI images of the same physical dimensions were fed as inputs to the pipeline. A 3D feature extractor was utilized to extract feature maps from the input images. Then, a fully connected layer was utilized to make age predictions as a regression task or a bucketed-classification task.

Data and preprocessing: We utilized the data collected in the Alzheimer's disease neuroimaging initiative (ADNI) study to validate our approach. For details see adni.loni.usc.edu/. ADNI is an ongoing longitudinal study that periodically collects imaging and blood biomarkers from elderly subjects who are at risk of developing dementia, primarily Alzheimer's disease (AD). The primary goal of ADNI has been to test whether serial magnetic resonance imaging (MRI), positron emission tomography (PET), other biological markers, and clinical and neuropsychological assessment can be combined to measure the progression of mild cognitive impairment (MCI) and early Alzheimer's disease. We analyzed 12,988 SMRI images of 1484 unique participants for whom ground truth information on their clinical stages of AD and chronological ages was available from the dataset. Clinical stages of AD consist of cognitively normal (CN), mild cognitive impairment (MCI), and Alzheimer's dementia (AD), and the ages are real numbers between 50 and 100. The dataset included multiple SMRI images taken at different time points, and corresponding ground truth information for some of the patients. The 3D SMRI images in this dataset were obtained using the MPRAGE sequence. Before performing model training, we resized the raw SMRI images to the same physical dimensions (voxel size), equalized their histograms, and cropped them to a shape of 256×256×256 (voxels) around the center.

Model description (FIG. 12): A 3D feature extractor based on an Inception-V1 network pretrained on the ImageNet dataset as described in J. Carreira and A. Zisserman, "Quo vadis, action recognition? a new model and kinetics dataset," in 2017 IEEE Conference on Computer Vision and Pattern Recognition (CVPR). IEEE 2017, pp. 4724-4733, was utilized to extract feature maps from the input images. One fully connected layer was used to generate age predictions. We predicted brain ages using a regressor and a bucketed classifier. In the bucketed-classification approach, the true ages of the subjects were binned into discrete ranges, and the neural network was used to predict the bin to which an SMRI image belonged. In our approach, we binned the ages into five buckets, 50-60, 60-70, 70-80, 80-90, and 90-100, and assigned them class labels in (1, 2, 3, 4, 5). These class labels were used during model training.

Evaluation: During model training, we utilized a fivefold cross-validation and patient-based stratification with 50% training, 25% tuning, and 25% testing fractions of the input dataset. Patient-based stratification was utilized to ensure that SMRI images of the same patient never appeared in more than one of the three datasets. Furthermore, the CNN-based models were trained using SMRI images of cognitively normal subjects only, i.e., the training and tuning sets included only cognitively unimpaired subjects. We took this approach to develop a baseline age predictor under healthy aging. Then, the trained models were used to predict the brain ages of a mixture of cognitively impaired and unimpaired subjects. While the regression model predicted real-number ages, the bucketed-classification approach predicted discrete values, i.e., one of (55, 65, 75, 85, 95). We included some cognitively unimpaired subjects in the testing set to maintain an unbiased testing sample. First, we evaluated model fit using the root of mean squared error (RMSE) metric achieved on the tuning set. Second, we evaluated the differences in brain age predictions between cognitively unimpaired and impaired subjects in the testing set. We performed that analysis using only the subjects in the testing dataset, and subjects at the MCI and AD clinical stages were considered to be cognitively impaired. We grouped the real-numbered predicted ages of the regression model based on the same ranges used for the bucketed-classification to come up with predicted age groups (see FIG. 14A).

Results

Figure 13A:
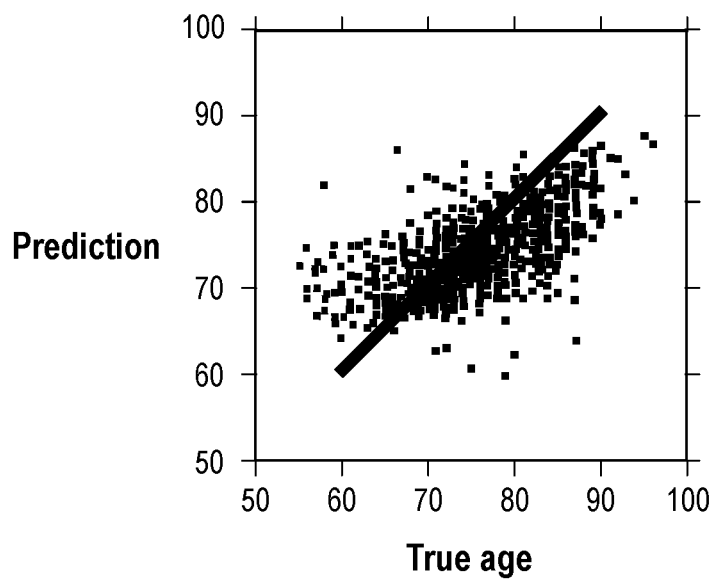
FIGS. 13A and 13B are scatter plots of predicted ages against true ages of cognitively normal subjects in the tuning dataset for the regression model and bucketed-classification model, respectively.
Figure 13B:
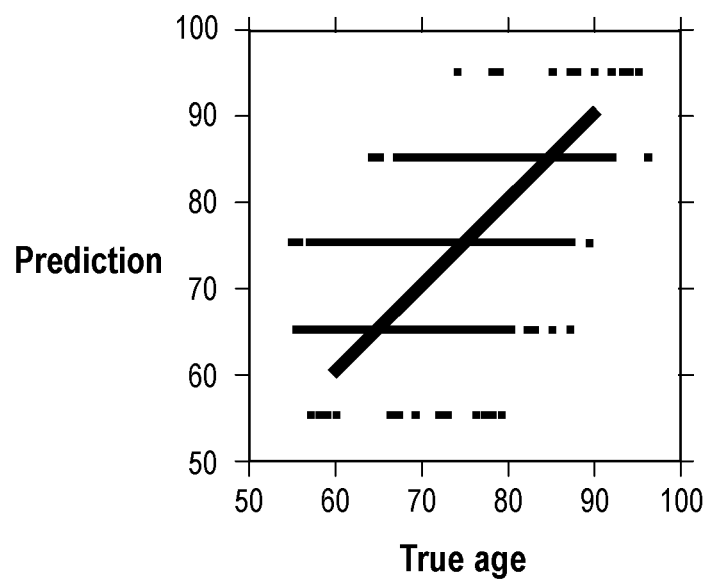
Figure 14A:
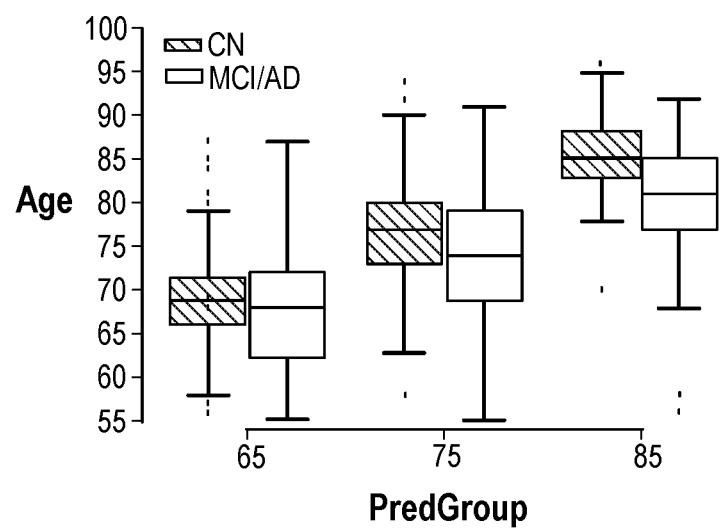
FIGS. 14A and 14B show box-plots of the distributions of true ages for cognitively unimpaired and impaired subjects in the same predicted age group. The figures show that the distribution of the true ages of cognitively impaired subjects consistently has a lower mean value than that of cognitively unimpaired subjects when they were predicted to be in the same age group. We excluded subjects with true ages <60 and >90, since there were not enough samples in the testing dataset. In addition, the predicted ages of cognitively impaired subjects were on average 3.24±2.12 and 2.67±2.35 years higher than their chronological ages in the regression and bucketed-classification approaches, respectively.
Figure 14B:
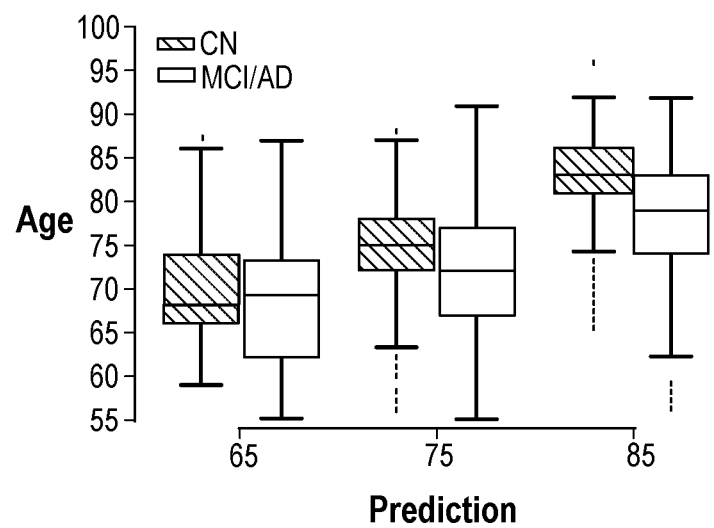

FIGS. 13*a* and 13*b* show scatter plots of predicted ages against true ages of cognitively normal subjects in the tuning dataset for the regression model and bucketed-classification model, respectively. The regression model achieved an RMSE of 5.54 while the bucketed-classification mode achieved an RMSE of 6.44. FIGS. 14*a* and 14*b* show box-plots of the distributions of true ages for cognitively unimpaired and impaired subjects in the same predicted age group. The figures show that the distribution of the true ages of cognitively impaired subjects consistently has a lower mean value than that of cognitively unimpaired subjects when they were predicted to be in the same age group. We excluded subjects with true ages <60 and >90, since there were not enough samples in the testing dataset. In addition, the predicted ages of cognitively impaired subjects were on average 3.24±2.12 and 2.67±2.35 years higher than their chronological ages in the regression and bucketed-classification approaches, respectively.

Conclusion

We developed two different convolutional neural network (CNN) based approaches based on the transfer-learning paradigm to predict brain ages from SMRI images. Our two models achieved RMSEs of 5.54 and 6.44 (years) in predicting brain ages of cognitively unimpaired subjects. Further analysis showed that there is a substantial difference between the predicted brain ages of cognitively impaired subjects and normal subjects who belong to the same chronological age group. Hence, we believe that predicted brain ages could prove to be clinically useful in identifying early in their lives the individuals who are at higher risk of developing aging-related brain diseases, such as Alzheimer's disease, early in their lives. In future work, we will obtain additional data to validate the findings and perform model optimization to improve prediction performance.

In one possible embodiment of this work, test can be performed to predict if a patient or subject is at higher risk of developing aging-related brain disease. The test makes use of a predictive model for brain age developed without domain knowledge from a data set of 30 images of cognitively impaired subjects and normal subjects who belong to the same chronological age group. The method includes step a) obtaining one or more 30 images from the patient and supplying the one or more 3D images to the predictive model; b) generating a brain age prediction for the subject with the predictive model, and c) comparing the brain age prediction with the actual age of the patient. If the brain age prediction is substantially greater than that of the actual age of the patient (a parameter that can be customized or adjusted, such as for example 3, 5 or 10 years), the patient is identified as being at increased risk of developing age-related brain disease, such as cognitive impairment or Alzheimer's disease. The criteria for "substantially greater" can be user specified, and possible examples are 7 or 10 years. The criteria would be expected to be a value that is greater than the margin of error of the model prediction.

While the Illustrated embodiment uses SMRI images for model generation and prediction, the methodology is also applicable to other 3D volumetric image data sets of the brain, such as for example CT scan images.

We claim:

1. A method for improving lung cancer screening and detection from a computed tomography data set obtained for a patient, comprising the steps of
    a) supplying the data set to a global predictive model comprising a three-dimensional deep convolutional neural network trained to predict at least the probability of the presence of cancer in lung tissue in the data set on a global basis, wherein the global predictive model includes an intermediate convolutional layer associated with a feature map;
    b) supplying the data set to a two-stage prediction model, the two-stage prediction model comprising
    1) a first stage detection model configured to detect the location of and generate respective cropped 3D volumes for one or more three-dimensional cancer candidates within the data set, and
    2) a second stage probability model operating on the one or more cropped 3D volumes for each of the one or more three-dimensional cancer candidates detected by the first stage detection model and assigning a cancer probability p to each of the three-dimensional cancer candidates, wherein the second stage probability model comprises an intermediate convolutional layer associated with a further feature map; and
    c) generating data representing (1) an overall prediction of the probability of cancer in the data set using both the prediction of the global predictive model and the cancer probabilities p assigned by the second stage probability model to each of the three-dimensional cancer candidates, wherein the overall prediction of the probability of cancer in the data set is obtained by either (i) appending the further feature map from the second stage model to the feature map of the intermediate convolutional layer of the global predictive model and generating the prediction from the global model, or (ii) appending the feature map from the global predictive model to the further feature map of the intermediate convolutional layer of the second stage model, and generating the prediction from the output of the second stage model, and (2) the location of cancer in the data set, wherein the location of cancer is determined by either the global predictive model or the two-stage prediction model.

2. The method of claim 1, wherein the one or more cropped 3D volumes for each of the one or more three-dimensional cancer candidates are provided to a plurality of second stage probability models operating on the one or more cropped 3D volumes for each of the one or more three-dimensional cancer candidates detected by the first stage detection model, each of the second stage probability models assigning a cancer probability p to each of the three-dimensional cancer candidates, wherein each of the plurality of second stage probability models are characterized by different model parameters.

3. The method of claim 2, wherein the different model parameters of the plurality of second stage probability models are selected from the group of parameters consisting of 1) different volumes of cropped 3D data in the data set, 2) different optimization parameters used during learning, 3) taking models at different points during the course of training, 4) different parameters as a result of data augmentation during training, 5) and different model architectural settings.

4. The method of claim 2, wherein in step c) the overall probability comprises an average of the global probability generated by the global predictive model, and the total probability for each of the candidates calculated by each of the plurality of second stage probability models.

5. The method of claim 2, wherein the plurality of second stage probability models comprise deep convolutional neural networks.

6. The method of claim 1, wherein the global predictive model is trained to predict at least one of the following in addition to the probability of presence of cancer in the data set:
    a) cancer outcome;
    b) presence of nodules of a size at least 20 mm in two dimensions;
    c) probability of mortality within 5 years; and
    d) diagnosis of lung cancer within 2 years.

7. The method of claim 1, wherein the global predictive model uses a base feature extractor to identify the presence of lung cancer in the data set and wherein the first stage detection model uses the base feature extractor.

8. The method of claim 1, wherein the first stage detection model and the second stage probability model comprise deep convolutional neural networks.

9. The method of claim 1, wherein first stage detection model operates on the whole volume of the data set.

10. The method of claim 1, wherein the global predictive model further comprises a lung segmentation feature identifying lung tissue within the data set such that the prediction of probability of presence of cancer in the data set globally operates only within the identified lung tissue.

11. The method of claim 1, further comprising the step of placing the overall prediction of the probability of cancer in the data set into a bucket of a risk stratification schema.

12. The method of claim 11, wherein the risk stratification schema approximates an existing risk stratification schema.

13. The method of claim 1, wherein either the global predictive model or the second stage probability model includes an attention mechanism.

14. The method of claim 13, wherein the attention mechanism comprises integrated gradients.

15. A computer-implemented system for improving lung cancer screening and detection from a computed tomography data set obtained for a patient, comprising in combination:
   a) a global predictive model comprising a three-dimensional deep convolutional neural network trained to predict at least the probability of the presence of cancer in lung tissue in the data set on a global basis, wherein the global predictive model includes an intermediate convolutional layer associated with a feature map;
   b) a two-stage prediction model, the two-stage prediction model comprising
      1) a first stage detection model configured to detect the location of and generate respective cropped 3D volumes for one or more three-dimensional cancer candidates within the data set, and
      2) a second stage probability model operating on the one or more cropped 3D volumes for each of the one or more three-dimensional cancer candidates detected by the first stage detection model and assigning a cancer probability p to each of the three-dimensional cancer candidates, wherein the second stage probability model comprises an intermediate convolutional layer associated with a further feature may; and
   c) a computer system executing code for generating data representing (1) an overall prediction of the probability of cancer in the data set using the prediction of the global predictive model and the cancer probabilities p assigned by the second stage probability model to each of the three-dimensional cancer candidates, wherein the overall prediction of the probability of cancer in the data set is obtained by either (i) appending the further feature map from the second stage model to the feature map of the intermediate convolutional layer of the global predictive model and generating the prediction from the global model, or (ii) appending the feature map from the global predictive model to the further feature map of the intermediate convolutional layer of the second stage model, and generating the prediction from the output of the second stage model, and (2) the location of cancer in the data set.

16. The system of claim 15, further comprising a plurality of second stage probability models operating on the one or more cropped 3D volumes for each of the one or more three-dimensional cancer candidates detected by the first stage detection model, each of the second stage probability models assigning a cancer probability p to each of the three-dimensional cancer candidates, wherein each of the plurality of second stage probability models are characterized by different model parameters.

17. The system of claim 16, wherein the different model parameters are selected from the group of parameters consisting of 1) different volumes of cropped 3D data in the data set, 2) different optimization parameters used during learning, 3) taking models at different points during the course of training, and 4) different parameters as a result of data augmentation during training.

18. The system of claim 15, wherein the overall probability comprises an average of the global probability generated by the global predictive model, and the total probability for each of the candidates calculated by each of the plurality of second stage probability models.

19. The system of claim 15, wherein the global predictive model is trained to predict at least one of the following in addition to the probability of presence of cancer in the data set:
   a) cancer outcome;
   b) presence of nodules of a size at least 20 mm in two dimensions;
   c) probability of mortality within 5 years; and
   d) diagnosis of lung cancer within 2 years.

20. The system of claim 15, wherein the global predictive model uses a base feature extractor to identify the presence of lung cancer in the data set and wherein the first stage detection model uses the base feature extractor.

21. The system of claim 15, wherein the first stage detection model and the second stage probability model comprise deep convolutional neural networks.

22. The system of claim 15, the computer system further executes code for placing the overall prediction of the probability of cancer in the data set into a bucket of a risk stratification schema.

23. The system of claim 15, wherein either the global predictive model or the second stage probability model includes an attention mechanism.

24. The system of claim 23, wherein the attention mechanism comprises integrated gradients.

25. A method for generating a deep learning system for increasing the specificity of lung cancer screening of computed tomography (CT) data sets, comprising the steps of
   a) training a global predictive model in the form of a three-dimensional deep convolutional neural network to predict at least the probability of the presence of cancer in lung tissue in a computed tomography data set, wherein the training is performed on a body of computed tomography data sets with ground truth annotations indicating presence or absence of cancer, and wherein the global predictive model includes an intermediate convolutional layer associated with a feature map;
   b) training a first stage detection model to detect the location of and generate respective cropped 3D volumes for one or more three-dimensional cancer candidates within the computed tomography data set;
   c) training a plurality of second stage probability models operating on the one or more cropped 3D volumes for each of the one or more three-dimensional cancer candidates detected by the first stage detection model, each of which assign a cancer probability p to each of the three-dimensional cancer candidates, wherein each of the plurality of second stage probability models are characterized by different model parameters, wherein each of the second stage probability models comprise an intermediate convolutional layer associated with a further feature map, and wherein the probability p is obtained by appending the feature map from the global predictive model to the further feature map of the intermediate convolutional layer of each of the second stage models, and generating the probability p from the output of the second stage models; and d) defining an algorithm for combining the predictions of the global predictive model and the second stage probability model in an ensemble manner to generate an ensemble prediction of the probability of cancer in a CT scan data set, wherein either the global predictive model or the two-stage model further is trained to identify the location of cancer in the CT scan data set.

26. The method of claim 25, wherein the different model parameters are selected from the group of parameters consisting of 1) different volumes of cropped 3D data in the data set, 2) different optimization parameters used during learning, 3) taking models at different points during the course of training, and 4) different parameters as a result of data augmentation during training.

27. The method of claim 25, wherein the algorithm is an average calculation.

28. The method of claim 25, wherein the global predictive model is trained to predict at least one of the following in addition to the probability of presence of cancer in computed tomography data set:

a) cancer outcome;
b) presence of nodules of a size at least 30 mm in two dimensions;
c) probability of mortality within 5 years; and
d) diagnosis of lung cancer within 2 years.

29. The method of claim 25, wherein the global predictive model incorporates a lung segmentation procedure to segment lung tissue from non-lung tissue in a computed tomography data set prior to generating a prediction of the probability of cancer in the lung tissue.

30. The method of claim 25, wherein either the global predictive model or the second stage probability models includes an attention mechanism.

31. The method of claim 30, wherein the attention mechanism comprises integrated gradients.

32. The method of claim 25, further comprising the step of defining a risk stratification schema in the form of a plurality of buckets wherein the overall prediction of the probability of cancer in the data set is placed into one of the buckets in the risk stratification schema.

33. The method of claim 32, wherein the risk stratification schema approximates an existing risk stratification schema.

* * * * *